(12) United States Patent
Kooij et al.

(10) Patent No.: US 11,590,311 B2
(45) Date of Patent: Feb. 28, 2023

(54) HEADGEAR WITH COVERED EDGE

(71) Applicant: ResMed Pty Ltd, Bella Vista (AU)

(72) Inventors: Michiel Kooij, Sydney (AU); Rupert Christian Scheiner, Sydney (AU); Annie Yu, Hong Kong (CN); Tzu-Chin Yu, Sydney (AU); Kit Lun Yick, Hong Kong (CN); Yiu Wan Yip, Hong Kong (CN); Jessica Lea Dunn, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 364 days.

(21) Appl. No.: 16/903,437

(22) Filed: Jun. 17, 2020

(65) Prior Publication Data

US 2020/0306481 A1 Oct. 1, 2020

Related U.S. Application Data

(63) Continuation of application No. 15/745,492, filed as application No. PCT/AU2016/050650 on Jul. 21, 2016, now Pat. No. 10,722,673.
(Continued)

(51) Int. Cl.
*A61M 16/06* (2006.01)
*A61F 9/02* (2006.01)
*A61M 16/10* (2006.01)

(52) U.S. Cl.
CPC ........ *A61M 16/0683* (2013.01); *A61F 9/02* (2013.01); *A61M 16/06* (2013.01);
(Continued)

(58) Field of Classification Search
CPC ............. A61M 16/0488; A61M 16/06; A61M 16/0611; A61M 16/0622; A61M 16/0633; A61M 16/0666; A61M 16/0672; A61M 16/0683; A61M 16/0688; A61M 16/0694; A61M 2205/0216; A62B 18/084;
(Continued)

(56) References Cited

U.S. PATENT DOCUMENTS

| 4,437,462 A | 3/1984 | Piljay |
| 4,782,832 A | 11/1988 | Trimble et al. |

(Continued)

FOREIGN PATENT DOCUMENTS

| CN | 2221804 Y | 3/1996 |
| CN | 2853007 Y | 1/2007 |

(Continued)

OTHER PUBLICATIONS

Second Chinese Office Action and English translation thereof dated Feb. 3, 2020 in corresponding CN Patent Application 201680043464,8.
(Continued)

*Primary Examiner* — Joseph D. Boecker
(74) *Attorney, Agent, or Firm* — Nixon & Vanderhye P.C.

(57) ABSTRACT

A headgear assembly includes a strap of a first flexible material with an elongate edge, and a second flexible material folded around and running along the elongate edge. The second flexible material may be an elastic material. The second flexible material may also cover an intersection or joint in the first flexible material such that the first flexible material may be made from two flexible materials layered together or joined end to end.

20 Claims, 43 Drawing Sheets

Related U.S. Application Data

(60) Provisional application No. 62/321,053, filed on Apr. 11, 2016, provisional application No. 62/196,329, filed on Jul. 24, 2015.

(52) U.S. Cl.
CPC .... *A61M 16/0611* (2014.02); *A61M 16/0633* (2014.02); *A61M 16/0688* (2014.02); *A61M 16/0694* (2014.02); *A61M 16/109* (2014.02); *A61M 2205/0216* (2013.01); *A61M 2210/0618* (2013.01)

(58) Field of Classification Search
CPC .... A61F 9/027; A61F 9/028; B63C 2011/128; A41D 13/1161
See application file for complete search history.

(56) References Cited

U.S. PATENT DOCUMENTS

| | | | |
|---|---|---|---|
| 4,944,310 | A | 7/1990 | Sullivan |
| 5,209,801 | A | 5/1993 | Smith |
| 6,532,959 | B1 | 3/2003 | Berthon-Jones |
| 6,581,594 | B1 | 6/2003 | Drew et al. |
| 6,861,379 | B1 | 3/2005 | Blaszczykiewicz |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2006/0081252 | A1 | 4/2006 | Wood |
| 2008/0235852 | A1 | 10/2008 | Ham |
| 2009/0044808 | A1 | 2/2009 | Guney |
| 2009/0050156 | A1 | 2/2009 | Ng et al. |
| 2010/0000534 | A1 | 1/2010 | Kooij et al. |
| 2010/0000544 | A1* | 1/2010 | Blaszczykiewicz ......... A61M 16/0683 428/221 |
| 2010/0229868 | A1 | 9/2010 | Rummery |
| 2010/0258136 | A1* | 10/2010 | Doherty ............ A61M 16/0683 24/595.1 |
| 2011/0072553 | A1 | 3/2011 | Ho |
| 2011/0197341 | A1* | 8/2011 | Formica ................ B32B 27/065 2/209.3 |
| 2012/0024290 | A1 | 2/2012 | Amarasinghe |
| 2012/0325219 | A1* | 12/2012 | Smith ............... A61M 16/0875 128/205.25 |
| 2013/0139822 | A1 | 6/2013 | Gibson |
| 2014/0026890 | A1 | 1/2014 | Haskard |
| 2014/0102456 | A1 | 4/2014 | Ovizinsky et al. |
| 2014/0158136 | A1 | 6/2014 | Romagnoli et al. |
| 2014/0190486 | A1 | 7/2014 | Dunn |
| 2015/0283348 | A1 | 10/2015 | Harp |
| 2015/0335848 | A1 | 11/2015 | Eury |
| 2016/0015923 | A1 | 1/2016 | Chodkowski |
| 2016/0067441 | A1 | 3/2016 | Bearne |
| 2016/0074614 | A1* | 3/2016 | Huddart ............. A61M 16/208 128/204.18 |
| 2016/0143766 | A1 | 5/2016 | Krishnasamy |
| 2018/0214655 | A1 | 8/2018 | Kooij et al. |

FOREIGN PATENT DOCUMENTS

| | | | |
|---|---|---|---|
| CN | 104524679 | A | 4/2015 |
| EP | 1 869 996 | A1 | 12/2007 |
| JP | 2012-511341 | A | 5/2012 |
| JP | 2014-517735 | A | 7/2014 |
| JP | 2014-532499 | A | 12/2014 |
| JP | 2015-119995 | A | 7/2015 |
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2009/148956 | A2 | 12/2009 |
| WO | WO 2010/066004 | A1 | 6/2010 |
| WO | WO 2010/135785 | A1 | 12/2010 |
| WO | WO 2012/171072 | A1 | 12/2012 |
| WO | WO 2013/020167 | A1 | 2/2013 |
| WO | WO 2013/175409 | | 11/2013 |
| WO | WO 2013/175409 | A1 | 11/2013 |
| WO | WO 2015/043119 | A1 | 4/2015 |
| WO | WO 2015/043229 | A1 | 4/2015 |

OTHER PUBLICATIONS

International Search Report for PCT/AU2016/050650, dated Dec. 5, 2016, 5 pages.
Written Opinion of the ISA for PCT/AU2016/050650, dated Dec. 5, 2016, 6 pages.
Written Opinion of the IPEA for PCT/AU2016/050650, dated Jul. 19, 2017, 7 pages.
International Preliminary Report on Patentability for PCT/AU2016/050650, dated Oct. 3, 2017, 13 pages.
"*Respiratory Physiology*", by John B. West, Lippincott Williams & Wilkins, 9$^{th}$ edition published 2012 (8 pages).
E.P Search Report dated Jan. 19, 2021 in corresponding EP application 20184210.1 (10 pages).
JP Notice of Allowance dated Mar. 29, 2021 in corresponding JP Application 2018-502694 (3 pages).
JP Notice of Reasons for Rejection and English translation thereof dated Jul. 27, 2020 in corresponding JP Application 2018-502694.
CN Decision of Rejection and English translation thereof dated Aug. 4, 2020 in corresponding CN Application 2016800434648.
Notice of Reasons for Rejection and English translation thereof dated Feb. 28, 2022 in corresponding JP Application P2021-074885 (10 pages).
Notice of Reexamination and English translation thereof dated Apr. 25, 2022 in corresponding CN Application 201680043464.8 (31 pages).

* cited by examiner

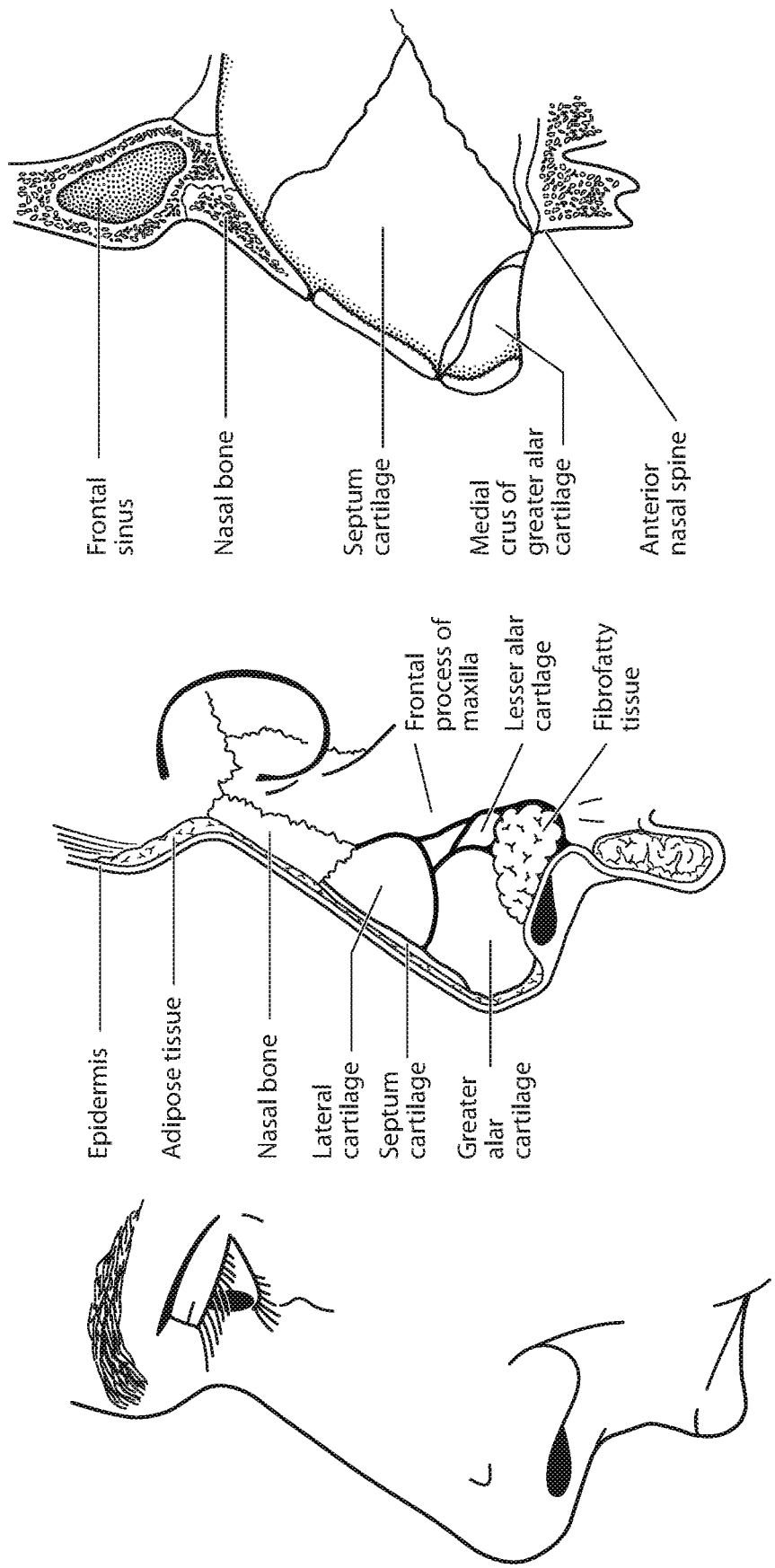

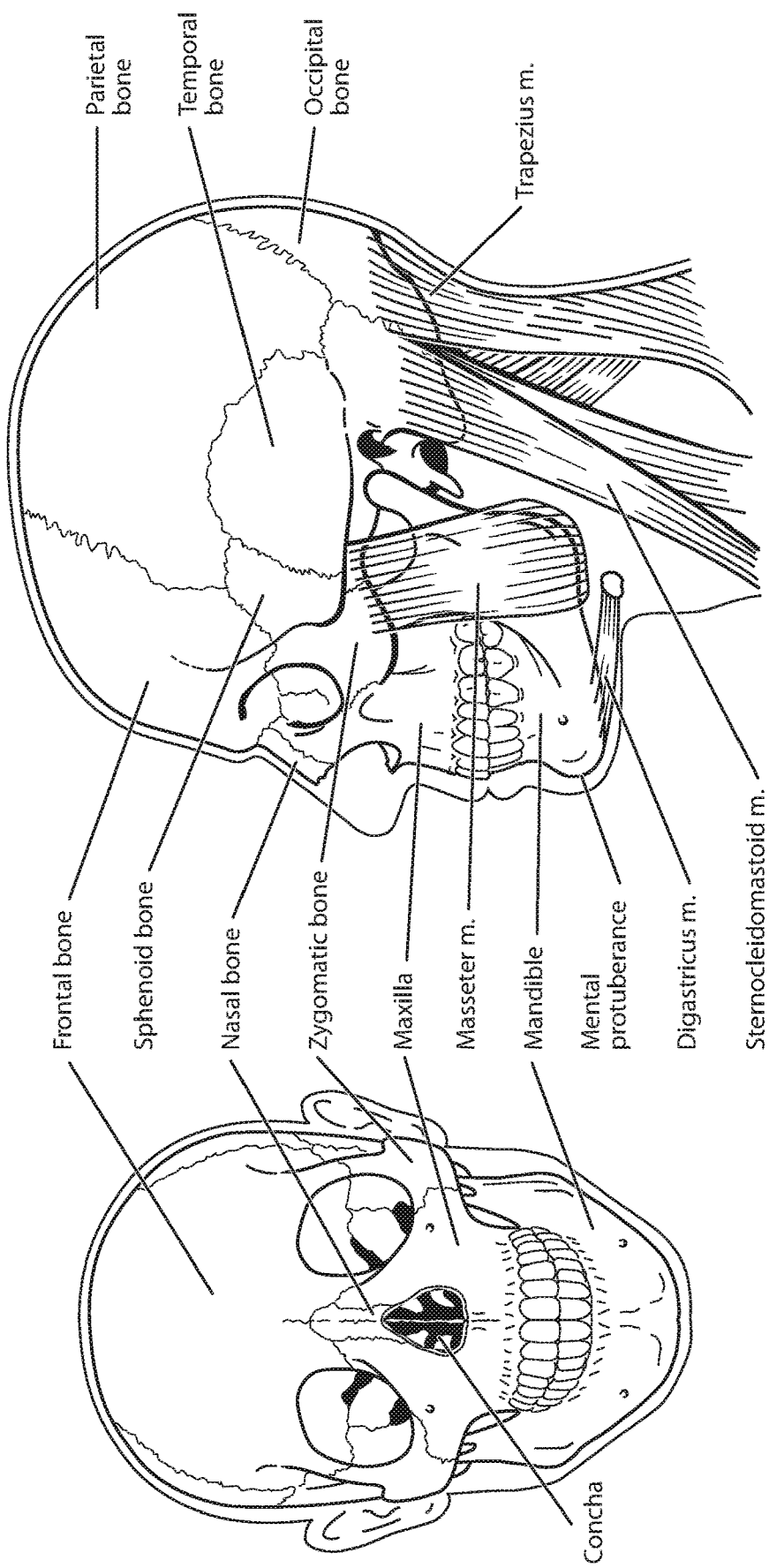

Relatively Large Positive Curvature

Relatively Small Positive Curvature

Zero Curvature

Relatively Small Negative Curvature

Relatively Large Negative Curvature

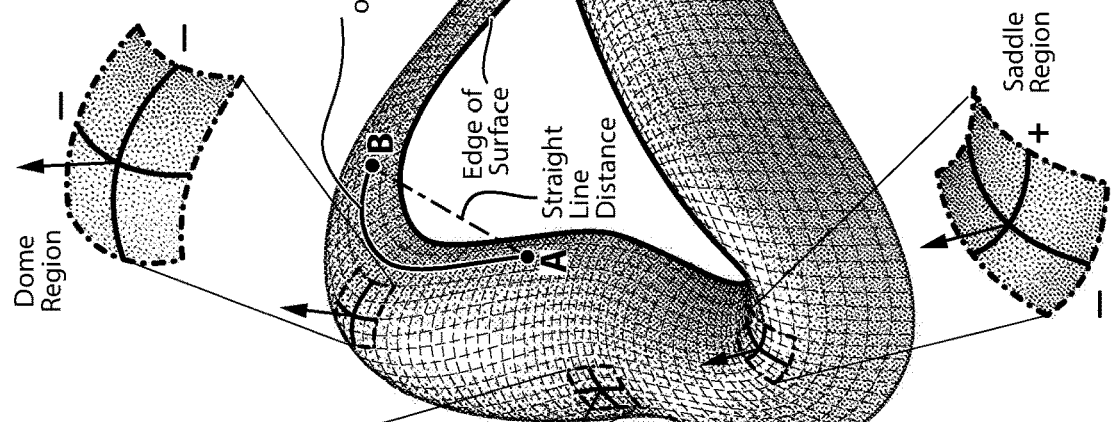
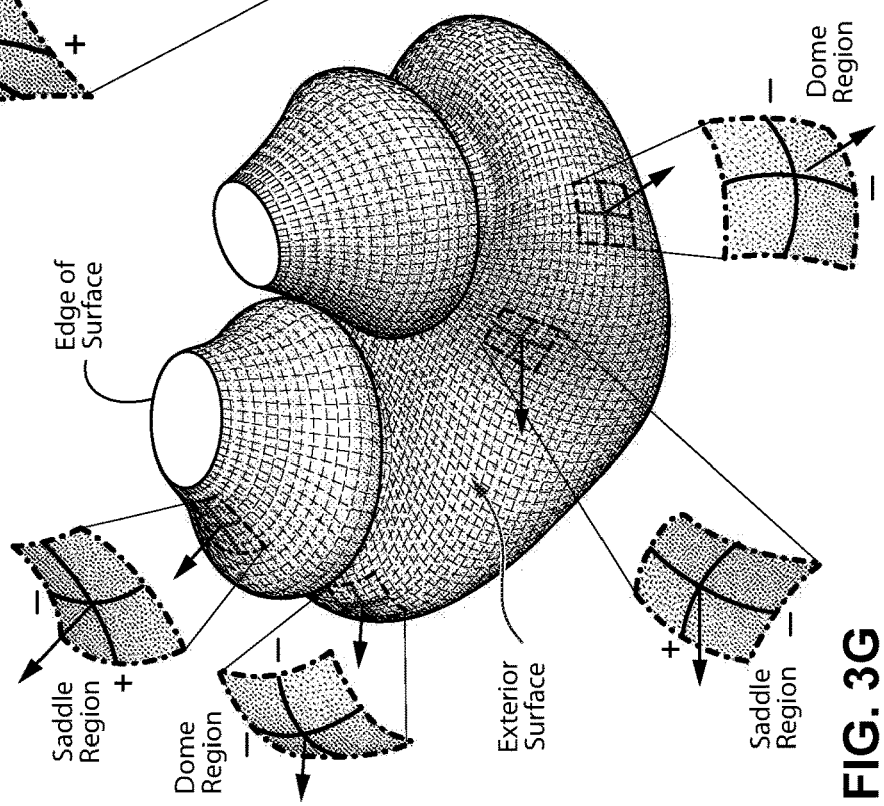
FIG. 3H
FIG. 3G

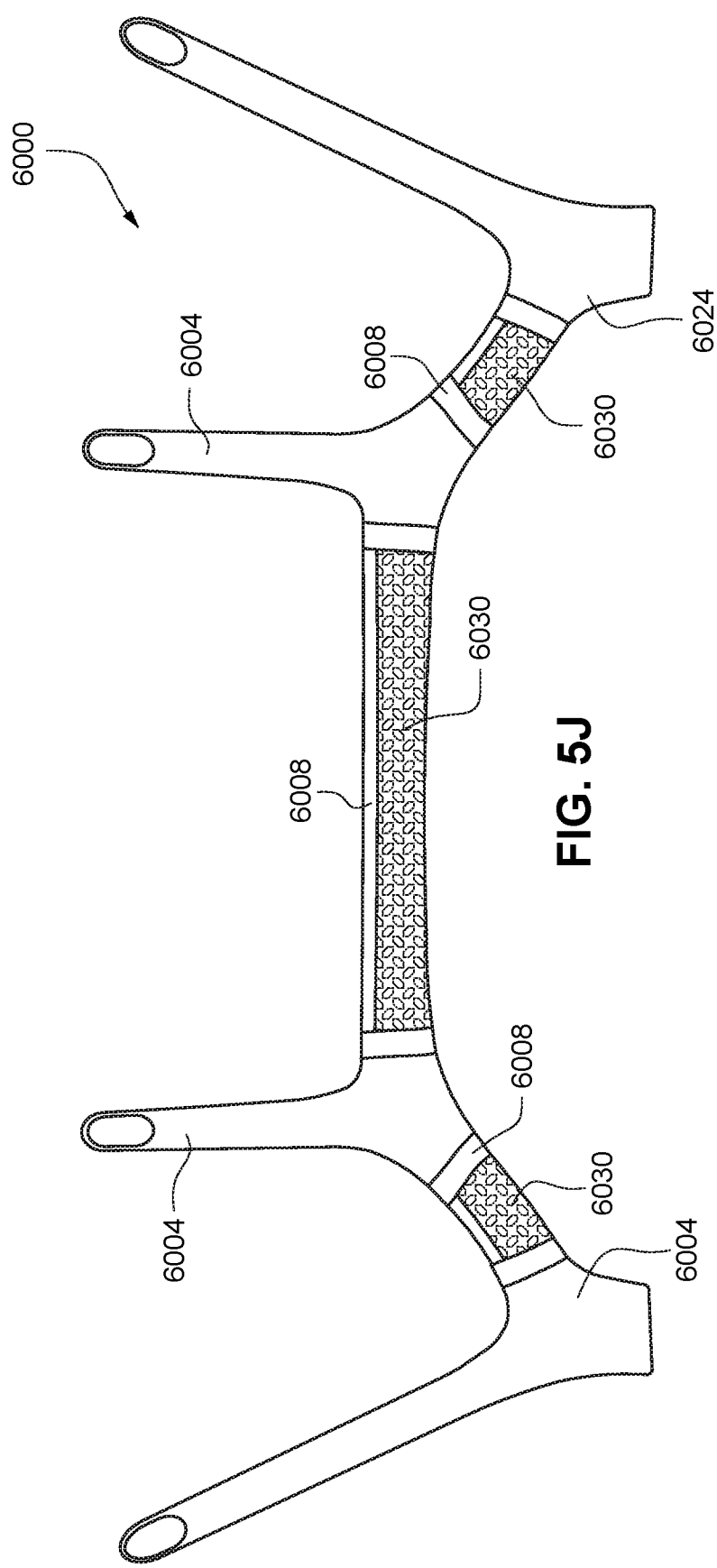

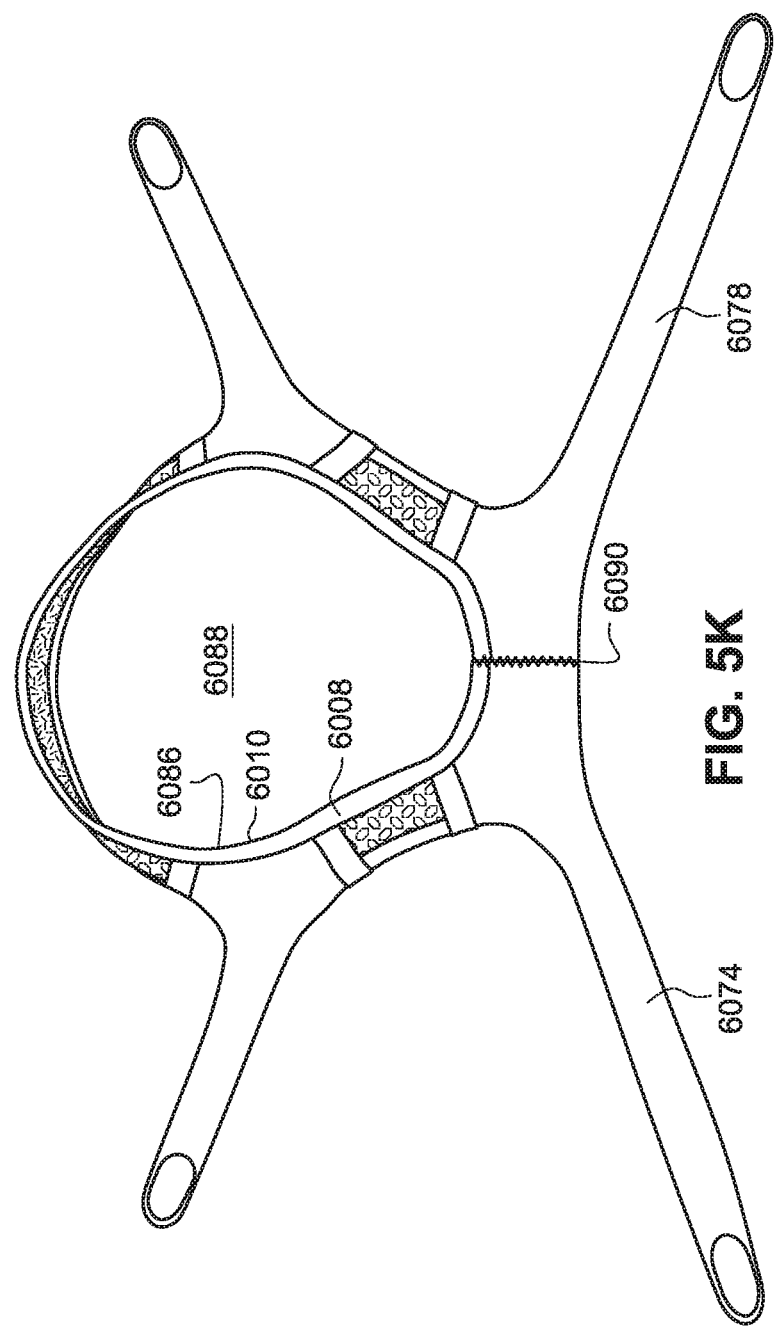

HEADGEAR WITH COVERED EDGE

This application is a continuation of U.S. patent application Ser. No. 15/745,492 filed Jan. 17, 2018, which is the U.S. national phase of International Application No. PCT/AU2016/050650 filed Jul. 21, 2016, which designated the U.S. and claims the benefit of U.S. Provisional Application No. 62/196,329, filed Jul. 24, 2015, and U.S. Provisional Application No. 62/321,053, filed Apr. 11, 2016, the entire contents of each of which are incorporated herein by reference.

1 BACKGROUND OF THE TECHNOLOGY

1.1 Field of the Technology

The present technology relates to headgear suitable for use in one or more of the detection, diagnosis, treatment, prevention and amelioration of respiratory-related disorders. The present technology also relates to medical devices or apparatus, and their use. For example, the headgear may be used with a mask specially adapted for the detection, diagnosis, treatment, prevention and amelioration of respiratory-related disorders.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory Insufficiency is an umbrella term for respiratory disorders in which patients are unable to ventilate enough to balance the $CO_2$ in their blood if their metabolic activity rises much above rest. Respiratory insufficiency may encompass some or all of the following disorders.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory insufficiency, in forms such as OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology comprises a headgear assembly comprising: a strap of a first flexible material with an elongate edge, and a second flexible material folded around and running along the elongate edge.

In examples, (a) the second flexible material is an elastic material; (b) the second flexible material is folded in a V-shape; (c) the first flexible material comprises a layer of a third flexible material and a layer of a fourth flexible material stacked and adhered together; (d) the second flexible material covers the third flexible material and the fourth flexible material such that edges of the stacked layers are covered; (e) the headgear assembly further comprises an adhesive film between the third flexible material and the fourth flexible material; (0 the first flexible material comprises woven material; (g) the first flexible material is a spacer fabric; (h) the elongate edge is rounded; (i) the strap comprises a second elongate edge that together with the elongate edge defines a width of the strap; (j) the headgear assembly further comprises a fifth flexible material folded around and running along the second elongate edge; (k) the second flexible material and the fifth flexible material are the same material; (l) the second flexible material extends across the width on a first side of the strap and is folded around and running along the second elongate edge; (m) the second flexible material does not cover all of the width on a second side of the strap (n) the second flexible material is attached to the strap; (o) the second flexible material is attached by adhesive on two sides of the strap; (p) the strap comprises a connection for a breathing mask; (q) the connection comprises a hole through which the breathing mask is configured to pass; (r) the hole is configured to pass around an outer perimeter of a section of the breathing mask; (s) the headgear assembly further comprises a sixth flexible material folded around and running along a perimeter of the hole; (t) the second flexible material and the sixth flexible material are the same material; and/or (u) a patient interface for delivering pressuring breathing gas to a patient, the patient interface comprising: a breathing mask and the headgear assembly according to any of the preceding examples.

An aspect of the present technology comprises a headgear assembly comprising: a first flexible strap portion with a first end; a second flexible strap portion with a second end attached to the first end to form a strap; and a covering material covering the attachment between the first end and the second end.

In examples, (a) the first flexible strap portion and the second flexible strap portion define an elongate edge of the strap and the covering material is folded over and along the elongate edge; (b) the first flexible strap portion and the second flexible strap portion define an elongate edge of the strap, the first end and the second end define short edges transverse to the elongate edge, and the covering material covers at least one of the short edges; (c) the first flexible strap portion and the second flexible strap portion define an elongate edge of the strap, the first end and the second end define short edges transverse to the elongate edge, the covering material covers at least one of the short edges, and the covering material is folded over and along the elongate edge; (d) the covering material covers an entire length of the at least one short edge; (e) the first flexible strap portion is configured to stretch more than the second flexible strap portion; (f) the first flexible strap portion is elastic and the second flexible strap portion is non-elastic; (g) the first flexible strap portion comprises a spacer fabric; (h) the second flexible strap portion comprises two layers of material at the second end and the first end is inserted between and connected to the two layers; (i) one of the two layers of material comprises a first half of a hook and loop fastener; (j) the second flexible strap portion further comprises a second half of a hook and loop fastener configured such that the second flexible strap portion can be folded to attach the first half of the hook and loop fastener to the second half of the hook and loop fastener; (k) the two layers of material are connected away from the second end beyond the first end; (l) the two layers form a Y-shape into which the first end is inserted; (m) the two layers of material are connect to each other and to the first end by layers of adhesive; (n) the strap comprises three legs that intersect to form a Y-shaped profile; (o) the headgear assembly further comprises a second strap releasably connected to the strap; (p) the second strap comprises a connection for a breathing mask; (q) the connection comprises a hole through which the breathing mask is configured to pass; (r) the hole is configured to pass around an outer perimeter of a section of the breathing mask; and/or (s) a patient interface for delivering pressuring breathing gas to a patient, the patient interface comprising: a breathing mask and the headgear assembly according to any of the preceding examples.

An aspect of one form of the present technology is a method of manufacturing apparatus.

An aspect of one form of the present technology is a method of manufacturing a headgear assembly comprising providing a first strap section made from a first fabric and having a first edge; providing a second strap section made from a second fabric and having a second edge; joining the first edge to the second edge at a joint; and covering the joint with a strip of a third fabric.

In examples, (a) the joint has a length and two ends and the strip covers the length; (b) the strip covers two sides of the length; (c) the strip is wrapped around the joint and covers the two ends; (d) the joint is a sewn joint; (e) the first strap section has a third edge that intersects the joint and the second strap section has a fourth edge that intersects the joint substantially at the third edge, and the method further comprises wrapping a second strip of the third fabric to extend along and around the third edge and the fourth edge; (f) the strip comprises at least one end that is covered by the second strip; (g) the method further comprises applying the second strip with a V-fold; (h) the first strap section has a third edge and the method further comprises providing a third strap section made from the second fabric and having a fourth edge; joining the third edge and the fourth edge at a second joint; and covering the second joint with another strip of the third fabric.

An aspect of certain forms of the present technology is a medical device that is easy to use, e.g. by a person who does not have medical training, by a person who has limited dexterity or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

3.2 Respiratory System and Facial Anatomy

Figure 1A:
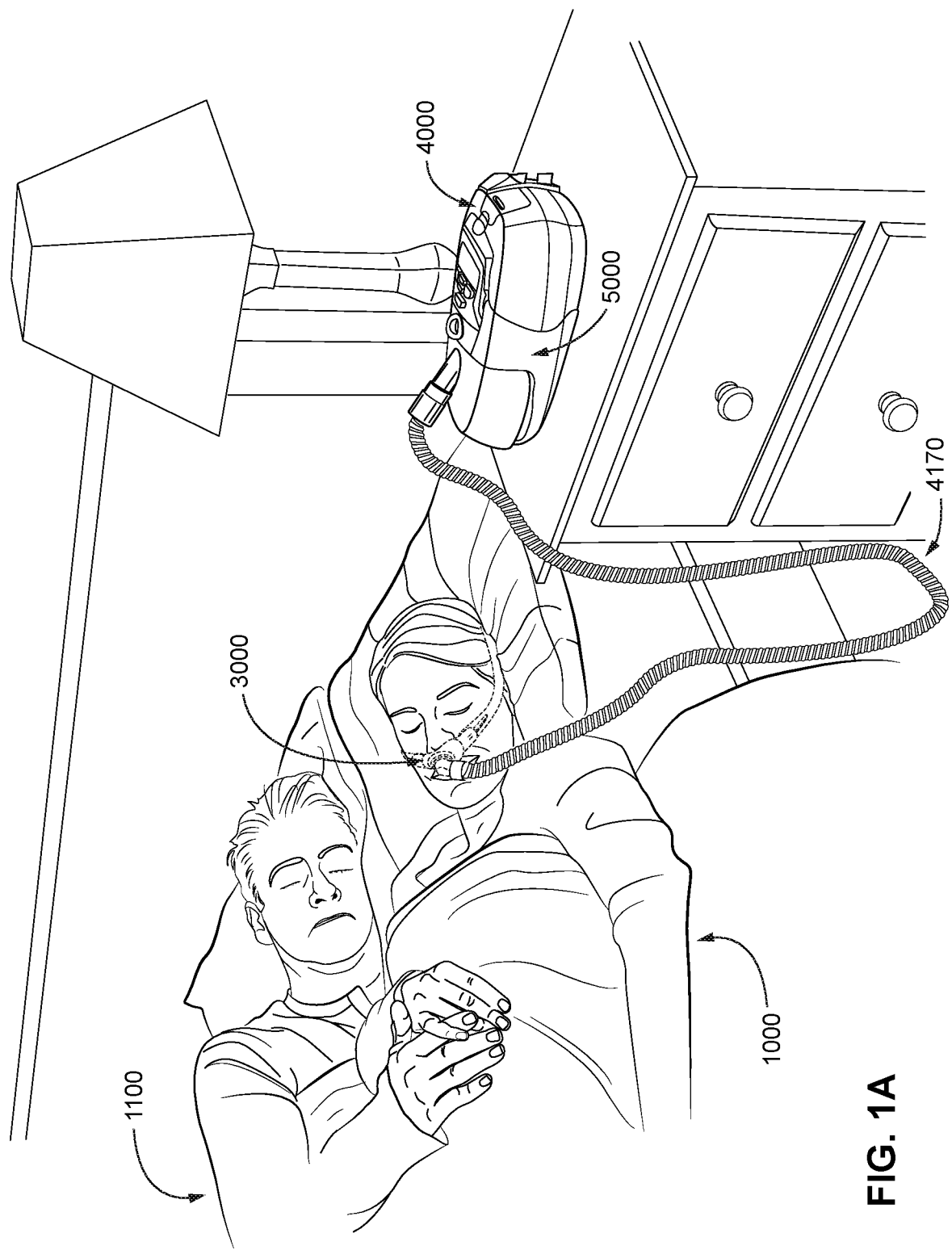
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
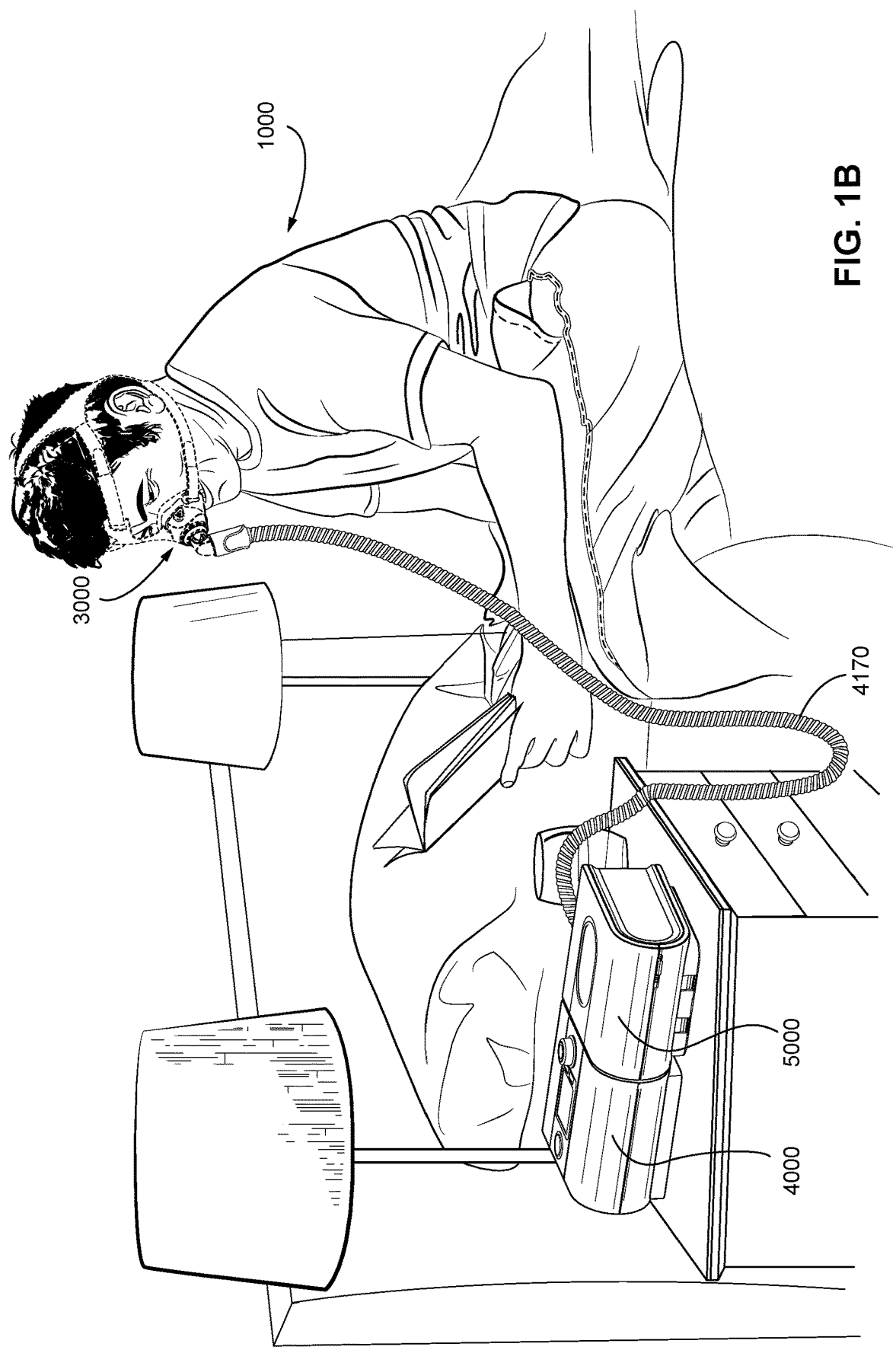
Figure 1C:
Figure 2A:
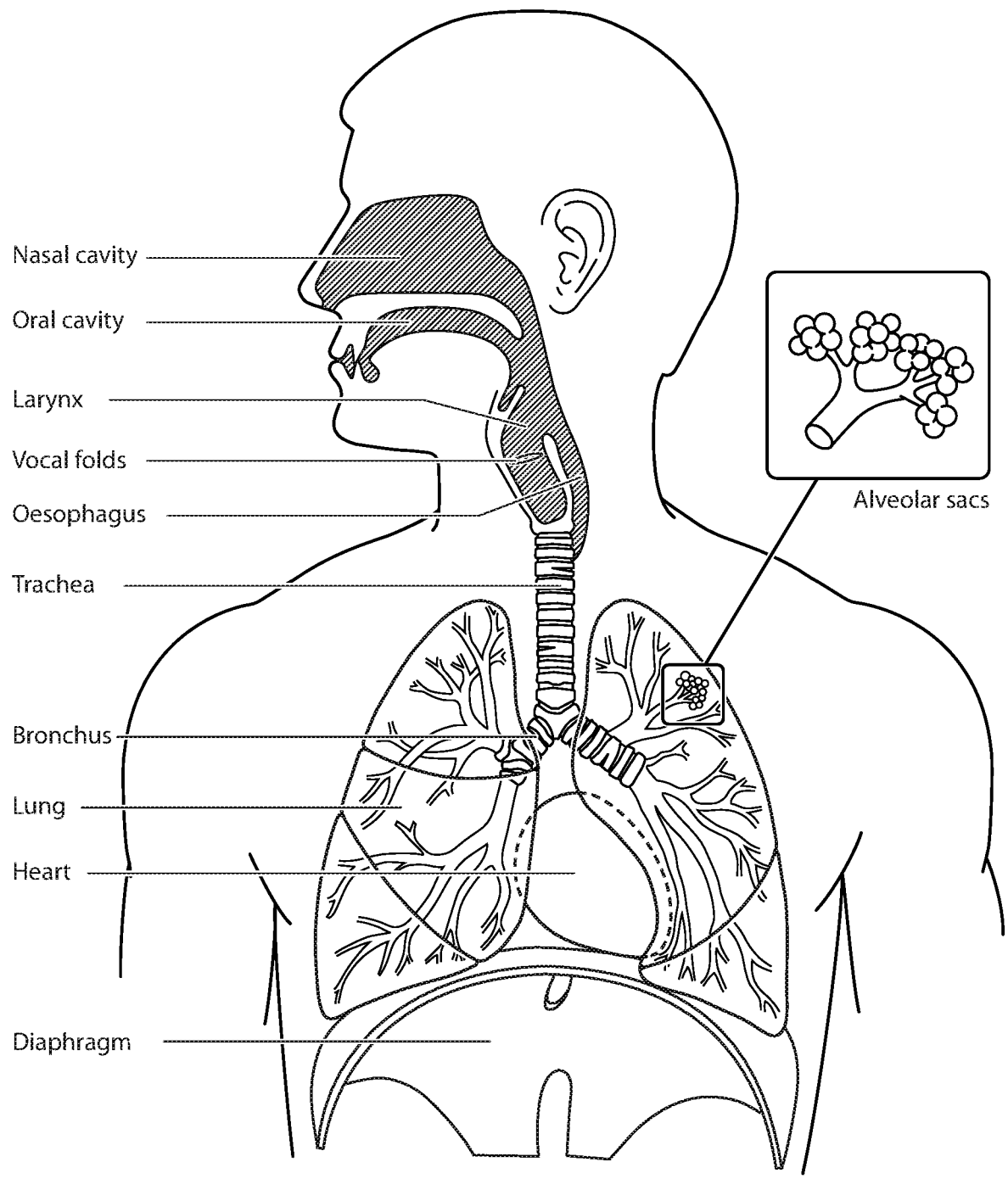

FIG. 2A shows an overview of a human respiratory system including the nasal and oral cavities, the larynx, vocal folds, oesophagus, trachea, bronchus, lung, alveolar sacs, heart and diaphragm.

Figure 2B:
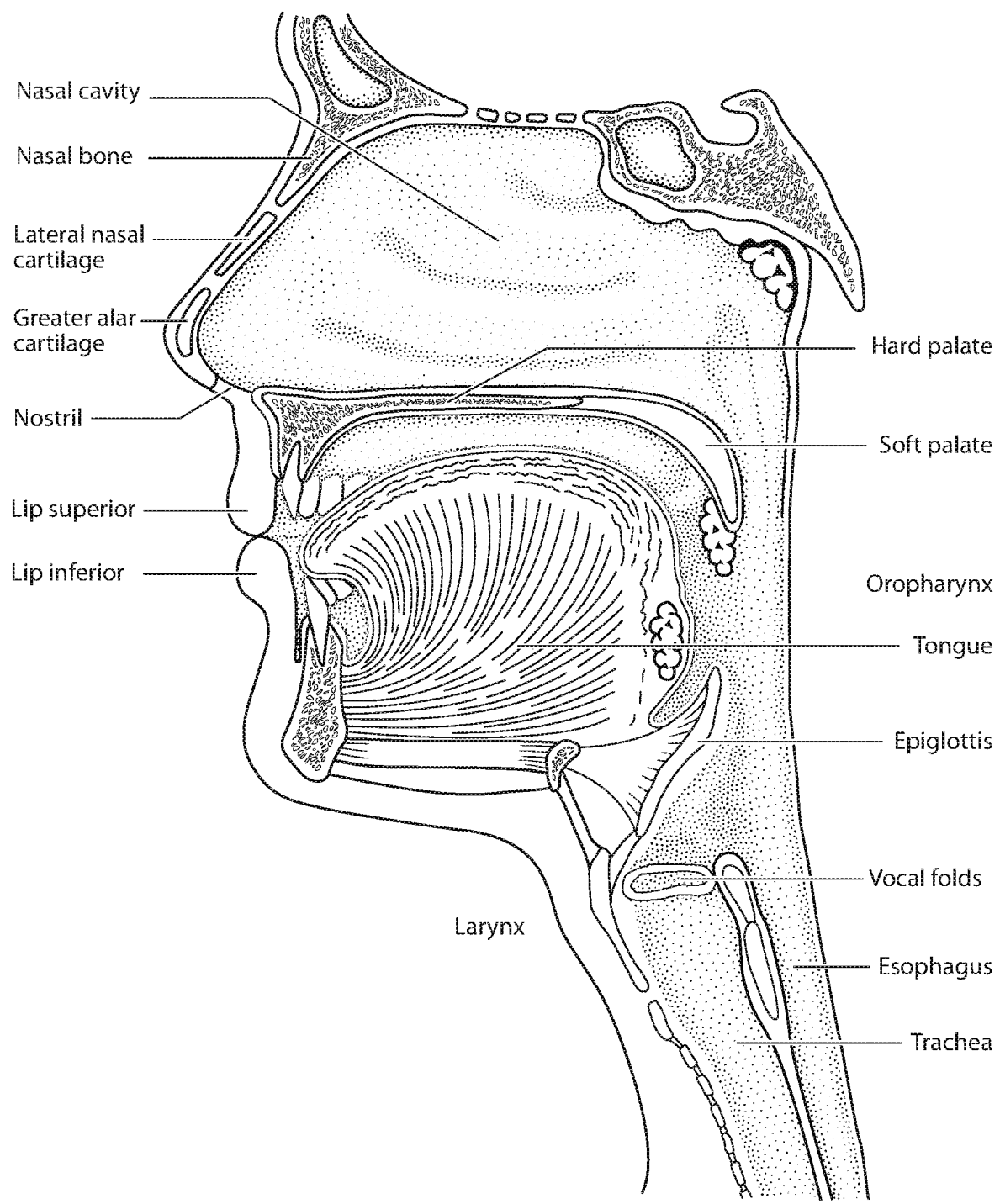

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
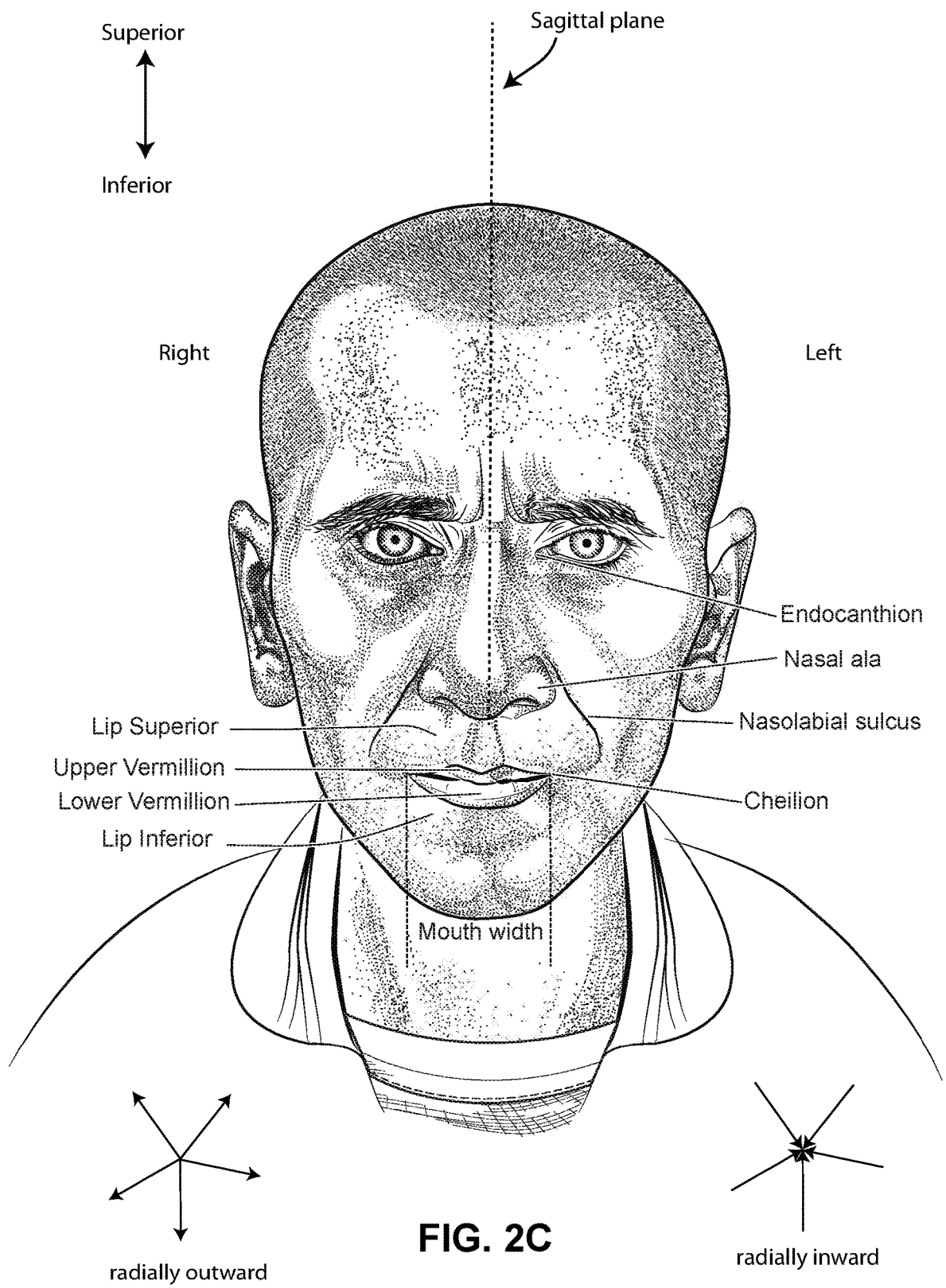

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
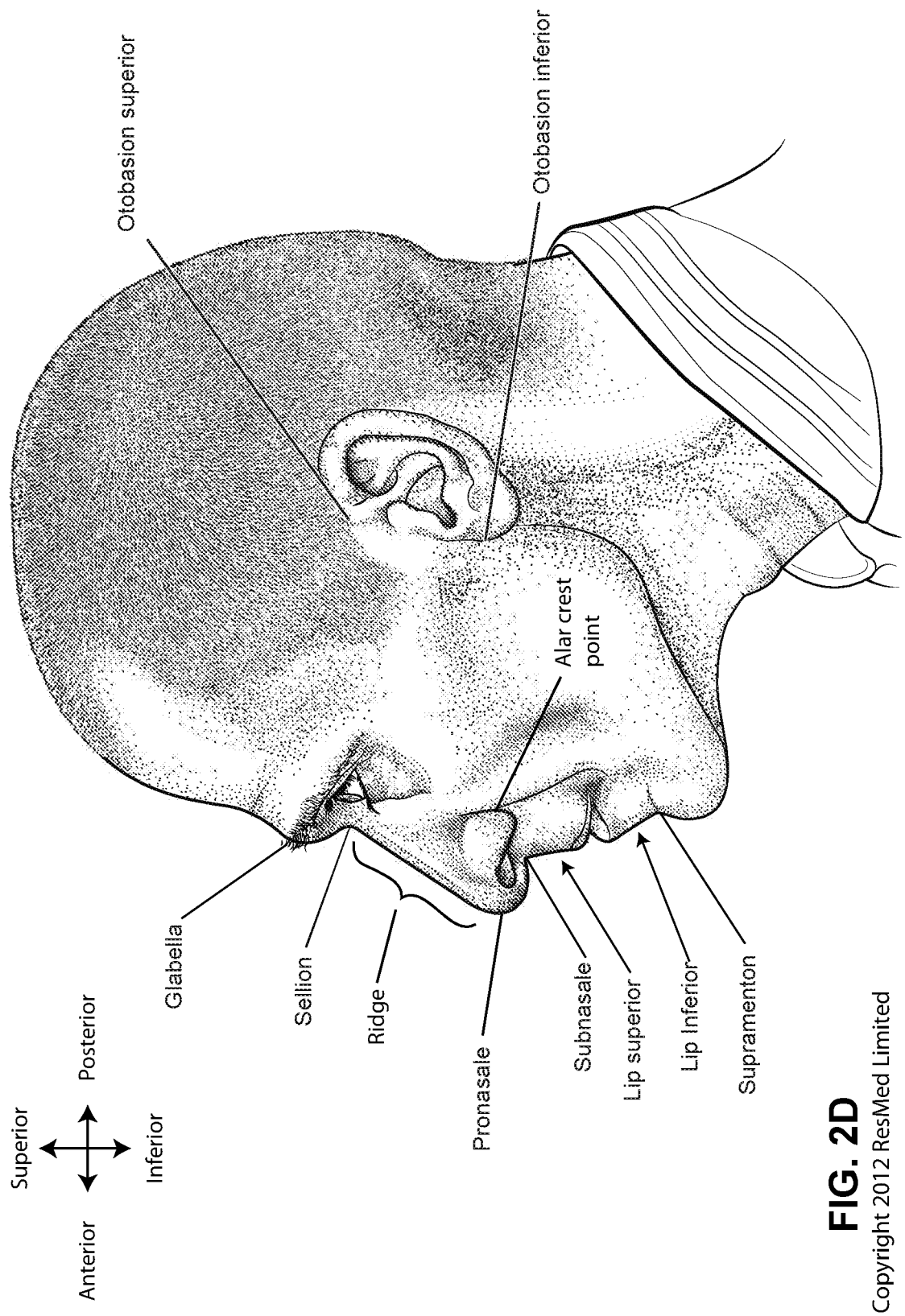

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
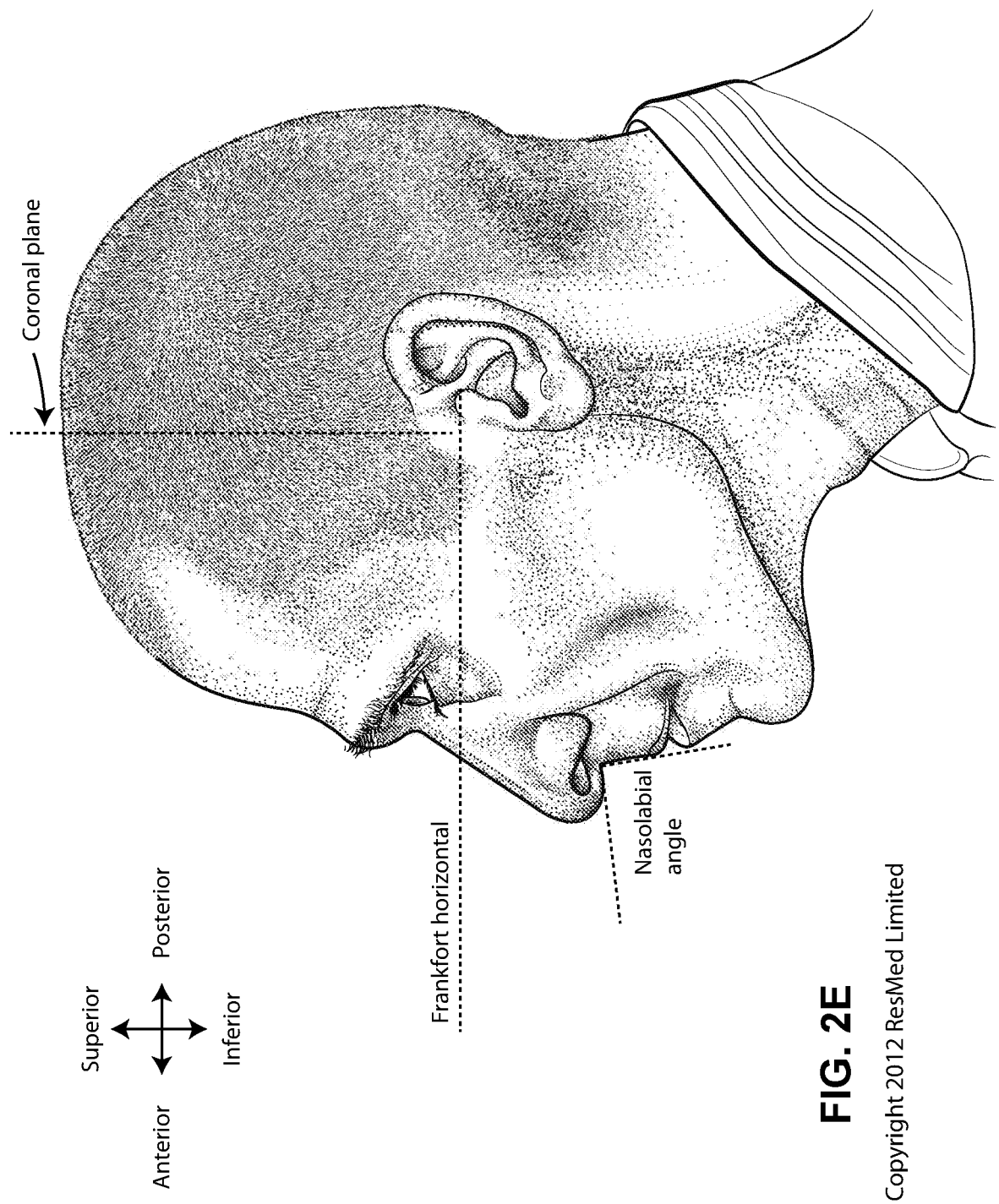

FIG. 2E is a further side view of a head. The approximate locations of the Frankfort horizontal and nasolabial angle are indicated. The coronal plane is also indicated.

Figure 2F:
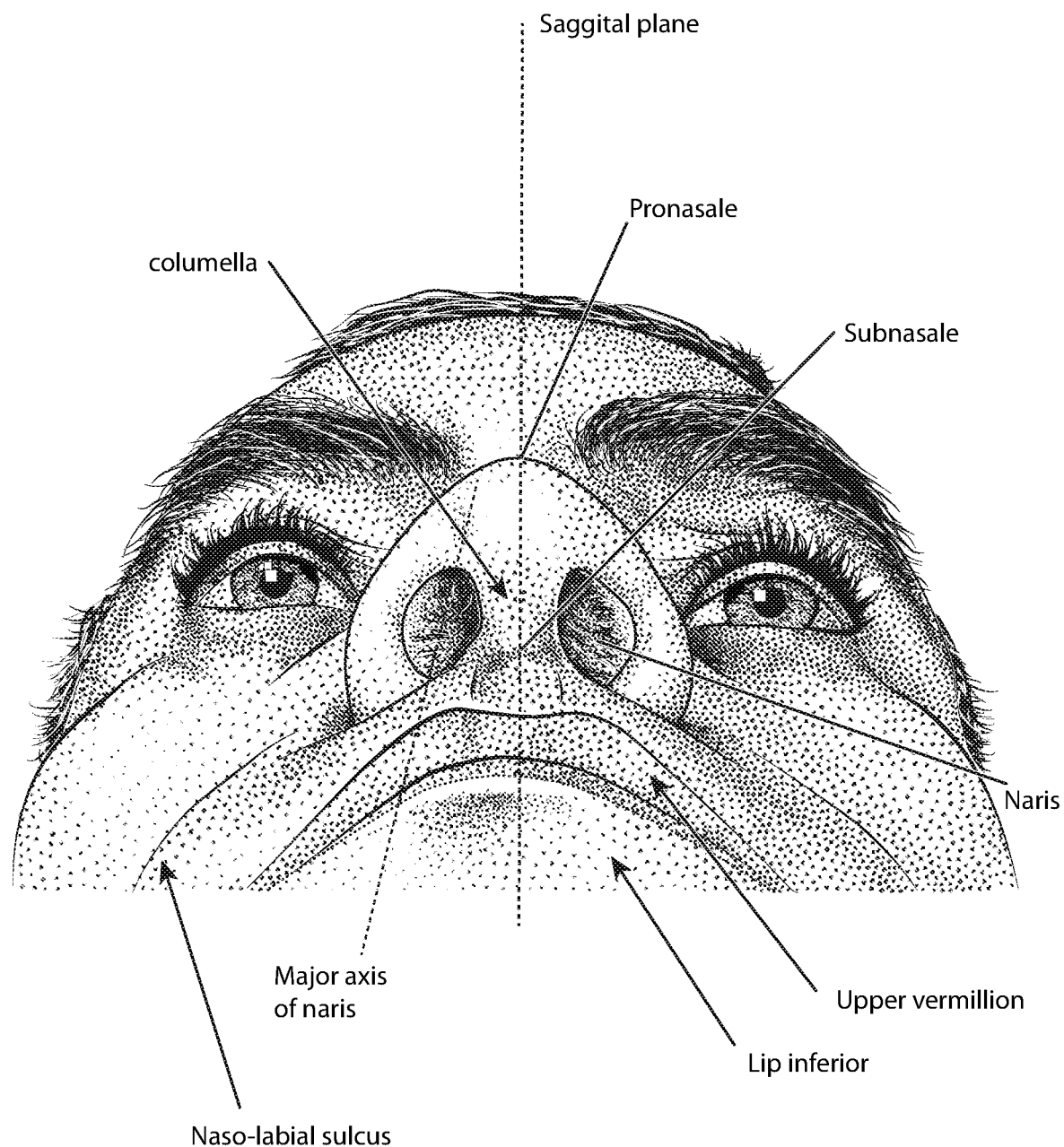

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
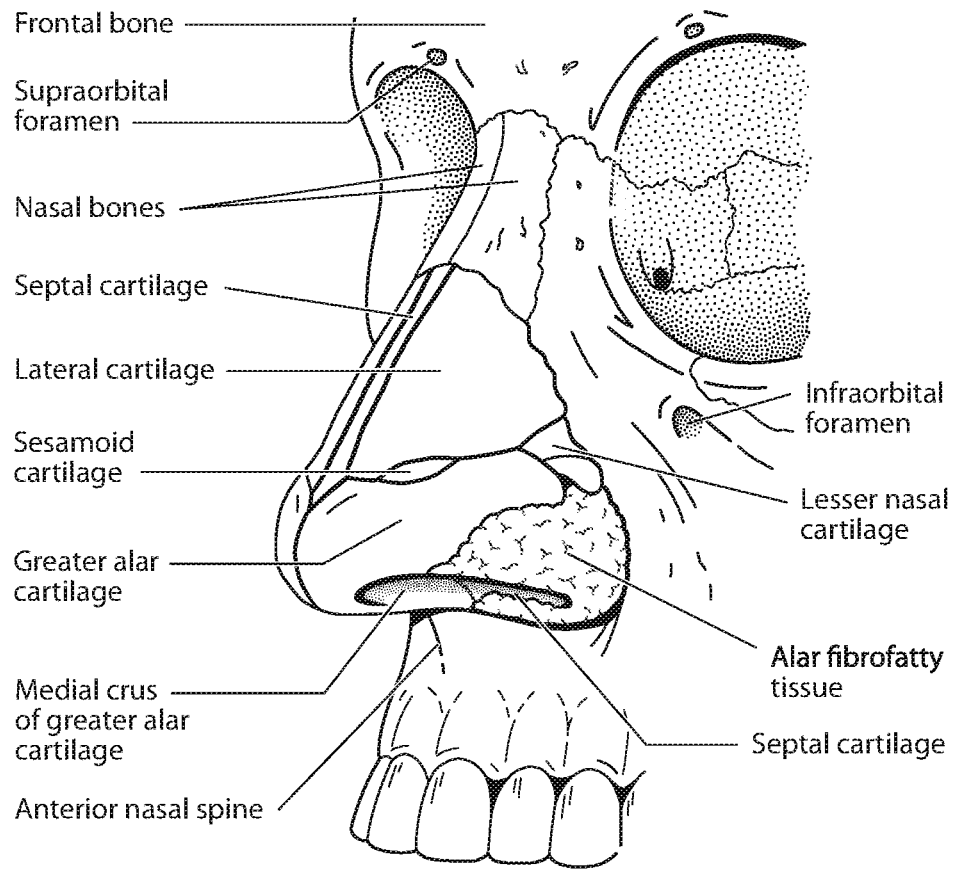

FIG. 2L shows an anterolateral view of a nose.

3.3 Patient Interface

Figure 3A:
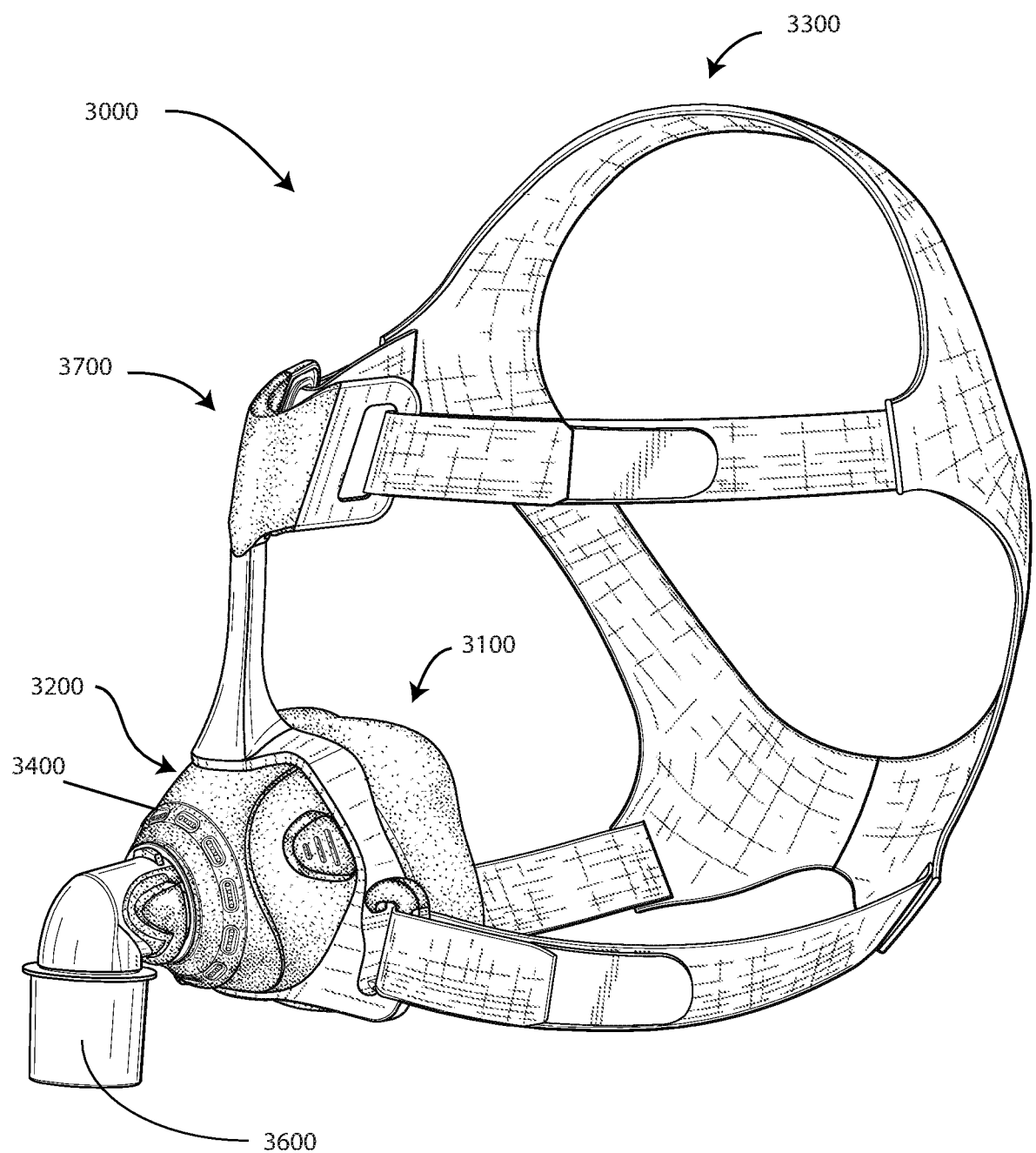

FIG. 3A shows a patient interface in the form of a nasal mask in accordance with one form of the present technology.

Figure 3B:
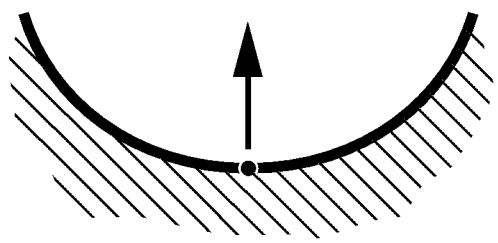

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
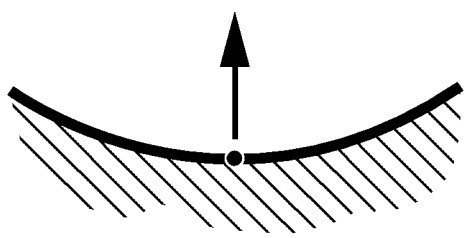

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
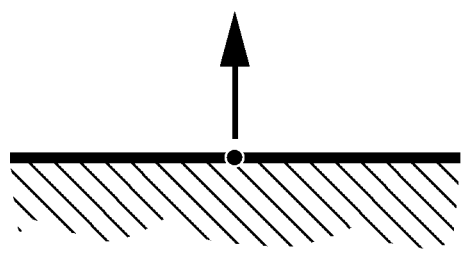

FIG. 3D shows a schematic of a cross-section through a structure at a point. An outward normal at the point is indicated. The curvature at the point has a value of zero.

Figure 3E:
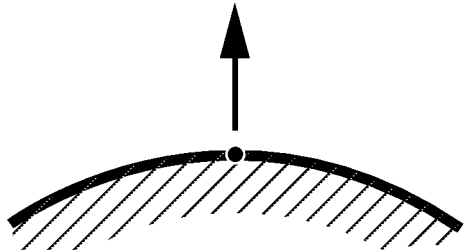

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
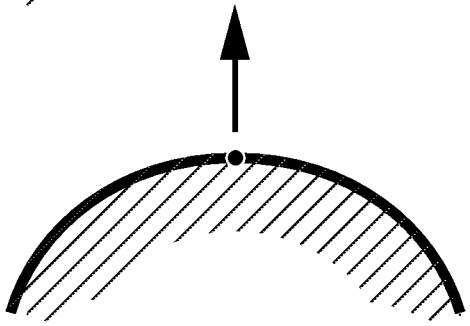

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

3.4 Headgear

Figure 4A:
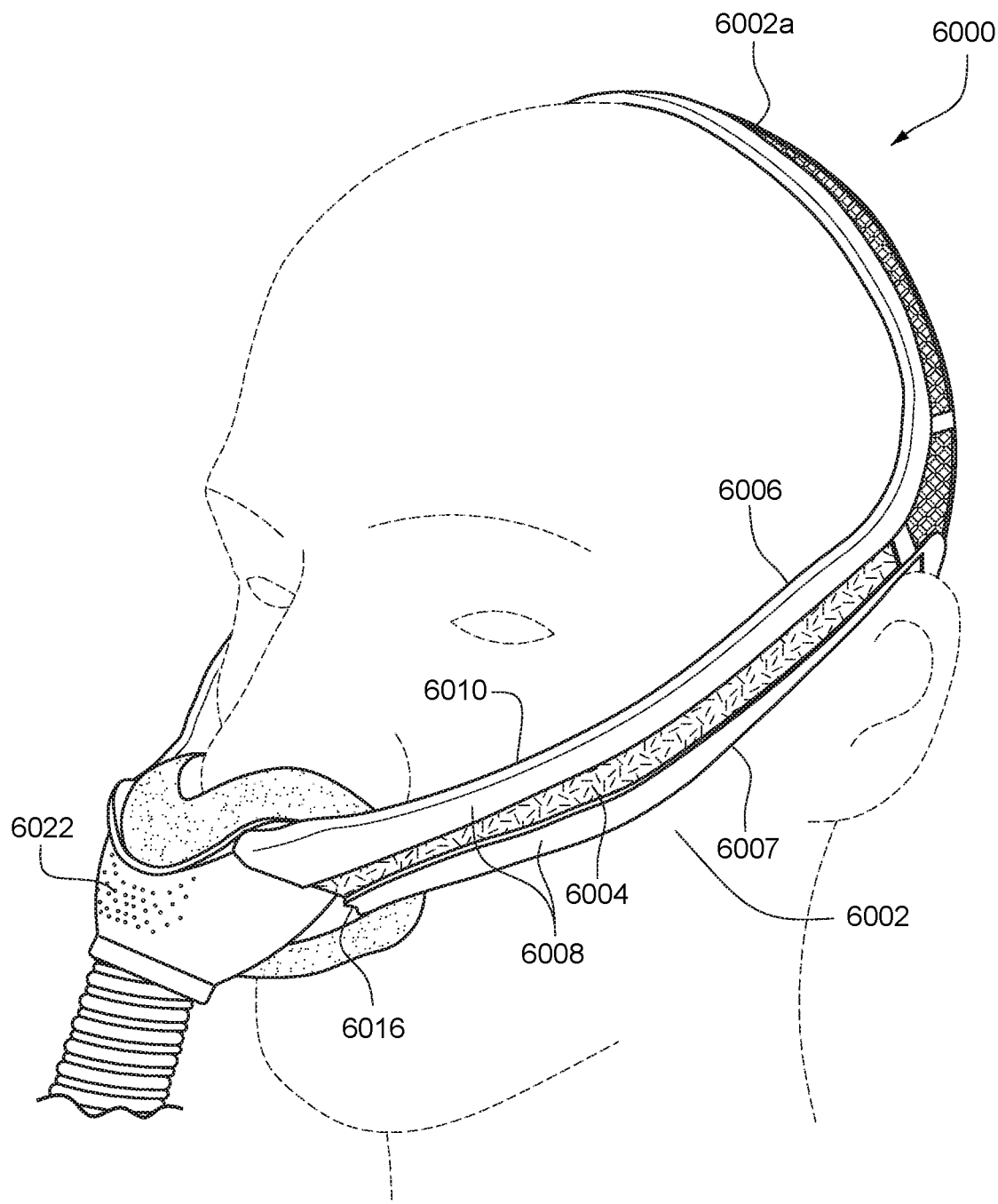

FIG. 4A shows a perspective view of headgear supporting a mask on a patient.

Figure 4B:
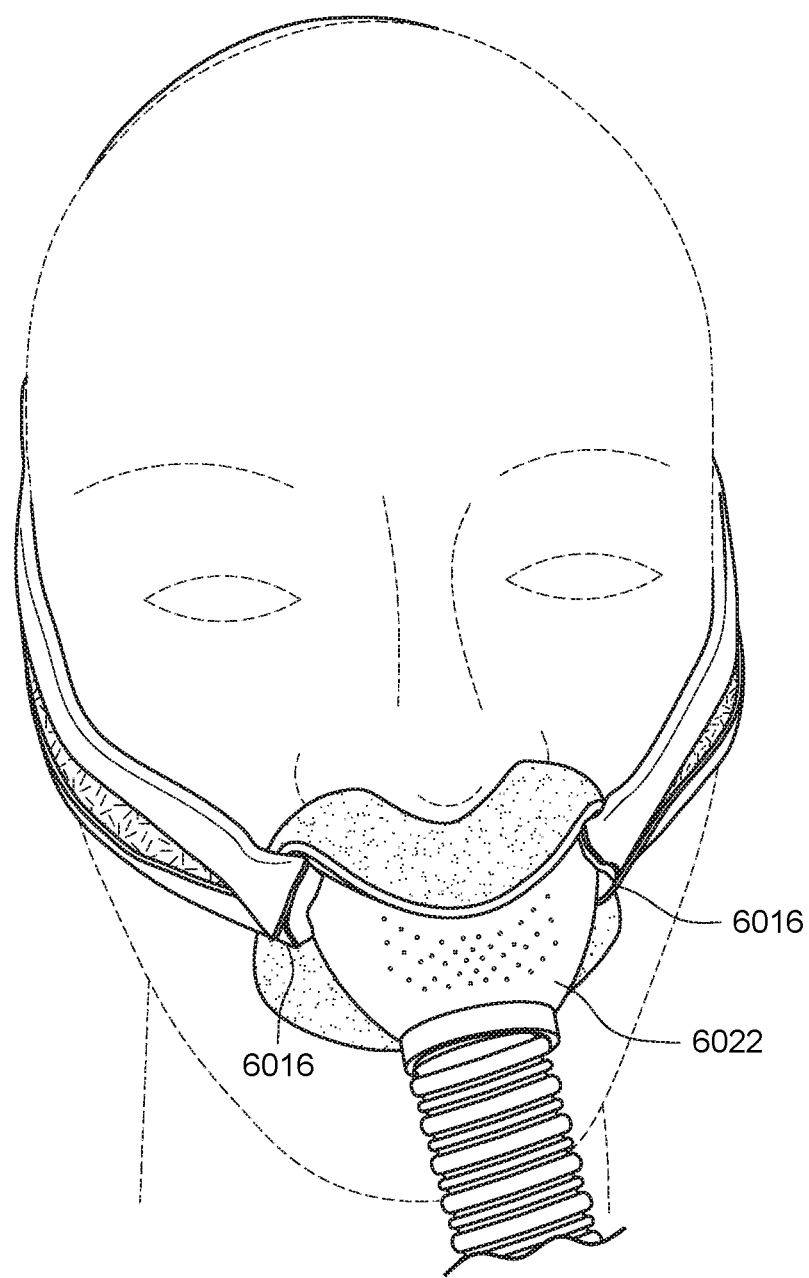

FIG. 4B shows a front view of headgear supporting a mask on a patient.

Figure 4C:
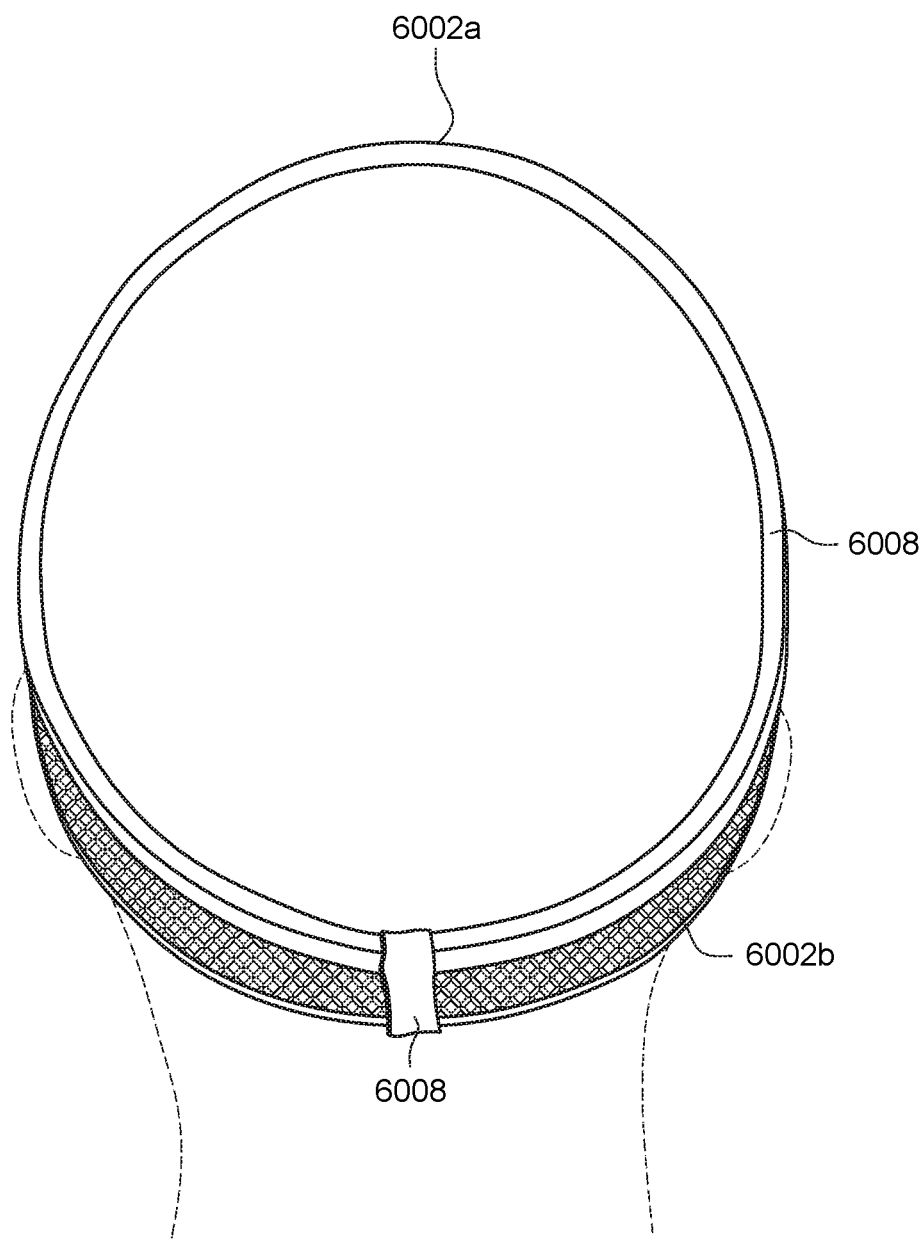

FIG. 4C shows a rear view of headgear supporting a mask on a patient.

Figure 4D:
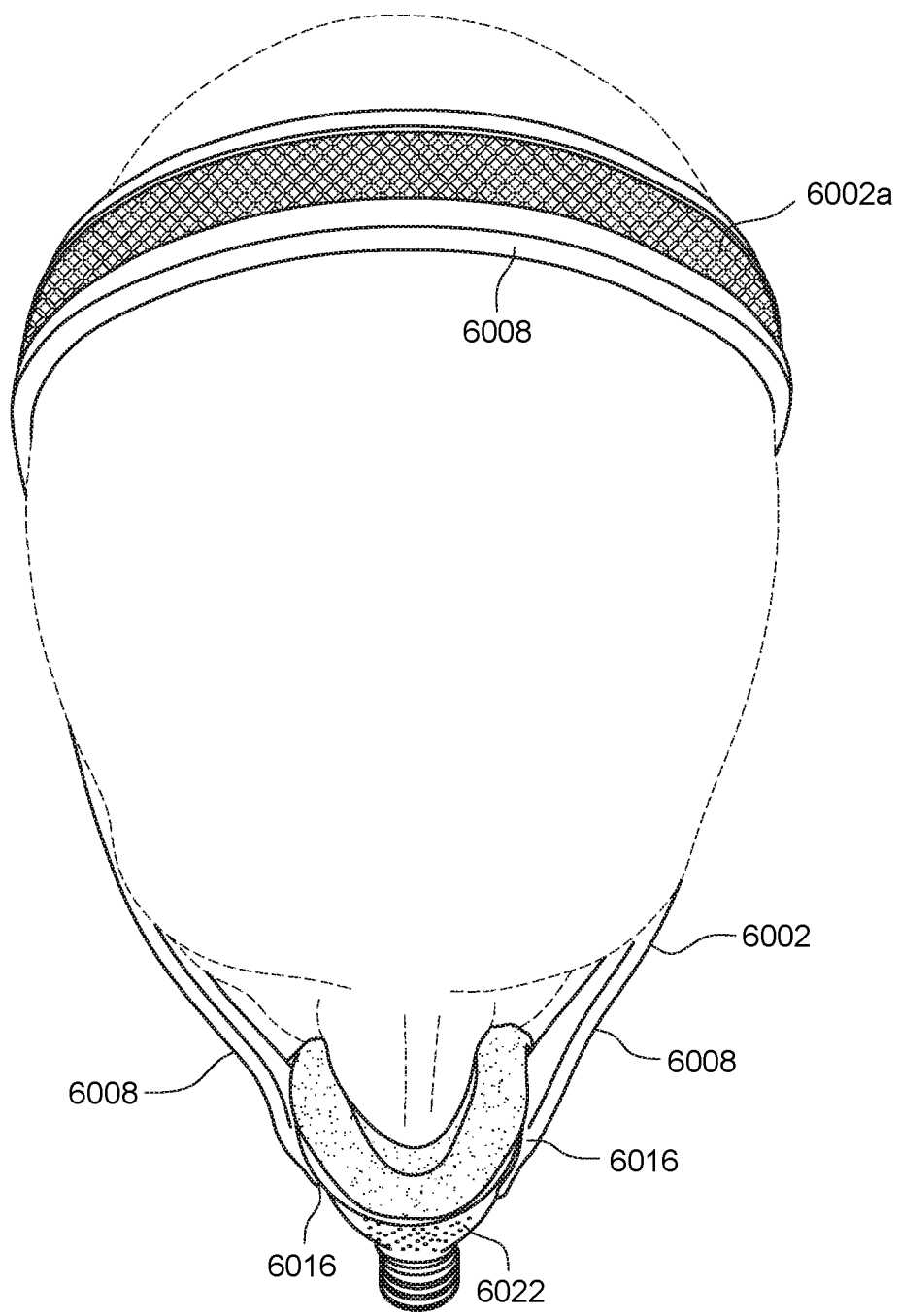

FIG. 4D shows a top view of headgear supporting a mask on a patient.

Figure 4E:
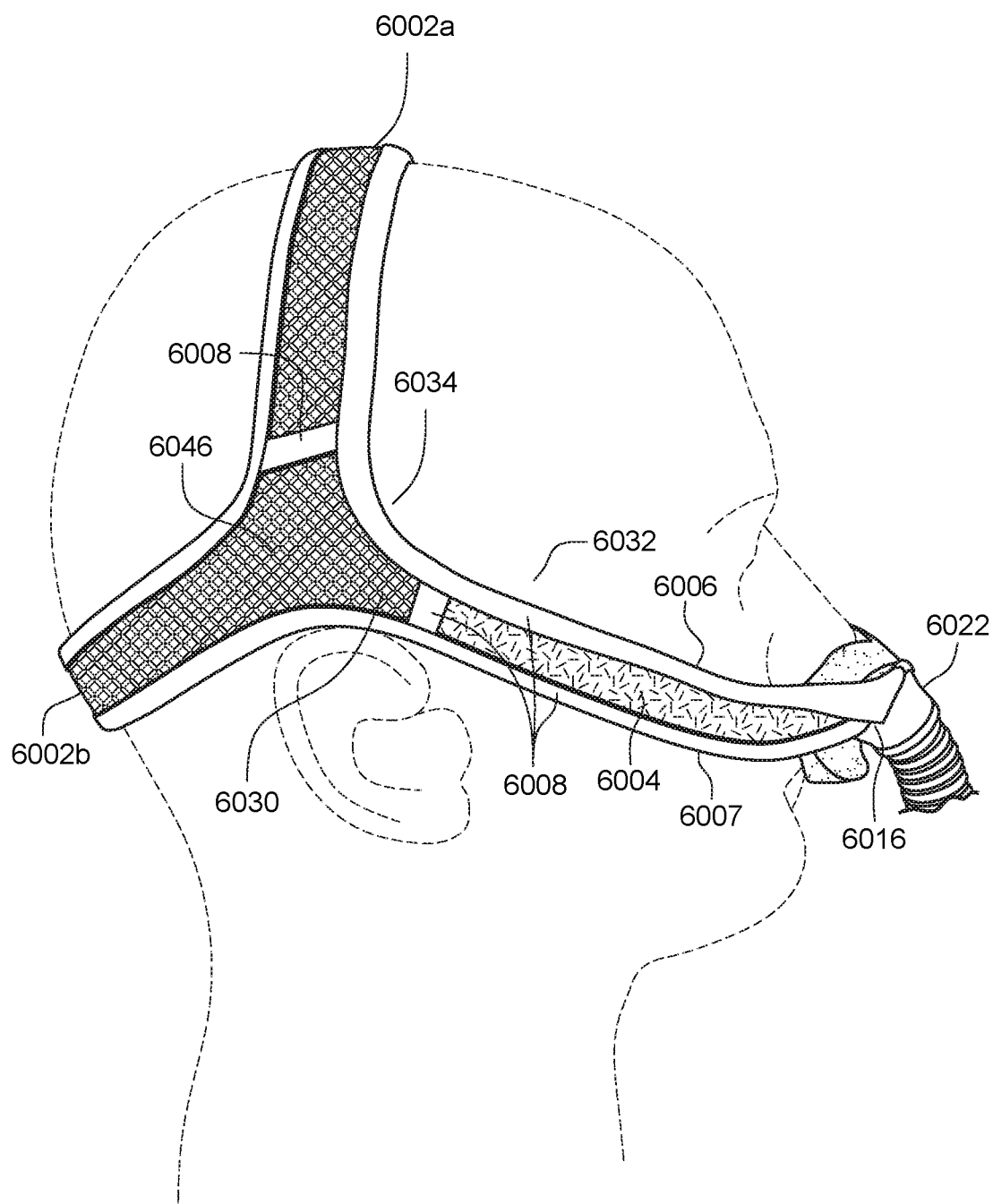

FIG. 4E shows a side view of headgear supporting a mask on a patient.

Figure 4F:
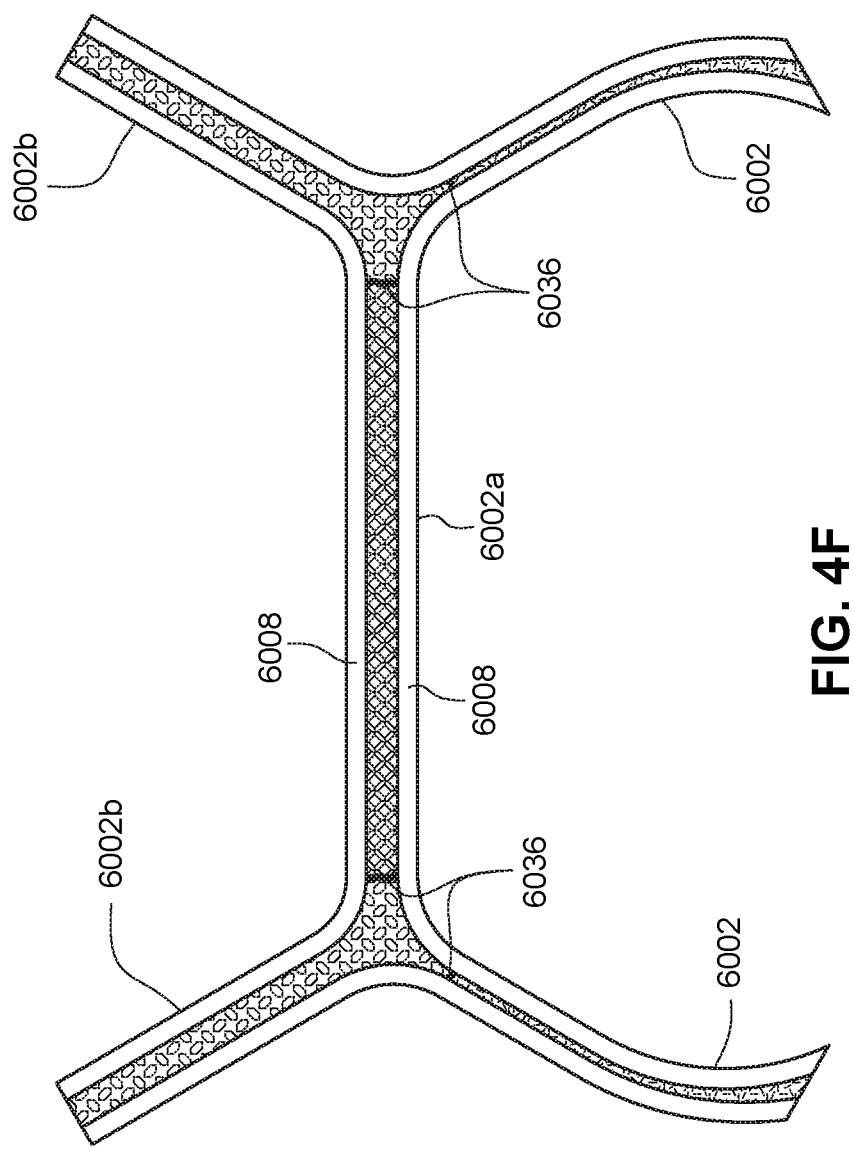

FIG. 4F shows headgear in a flat condition without a mask or connection to a mask.

Figure 4G:
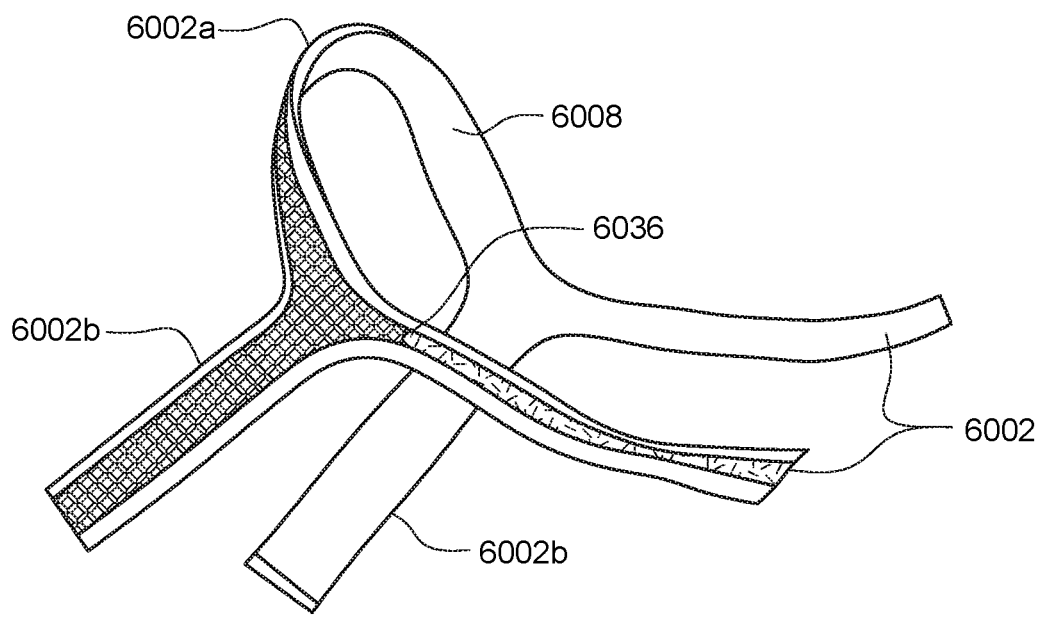

FIG. 4G shows the headgear of FIG. 4F in a folded condition.

Figure 4H:
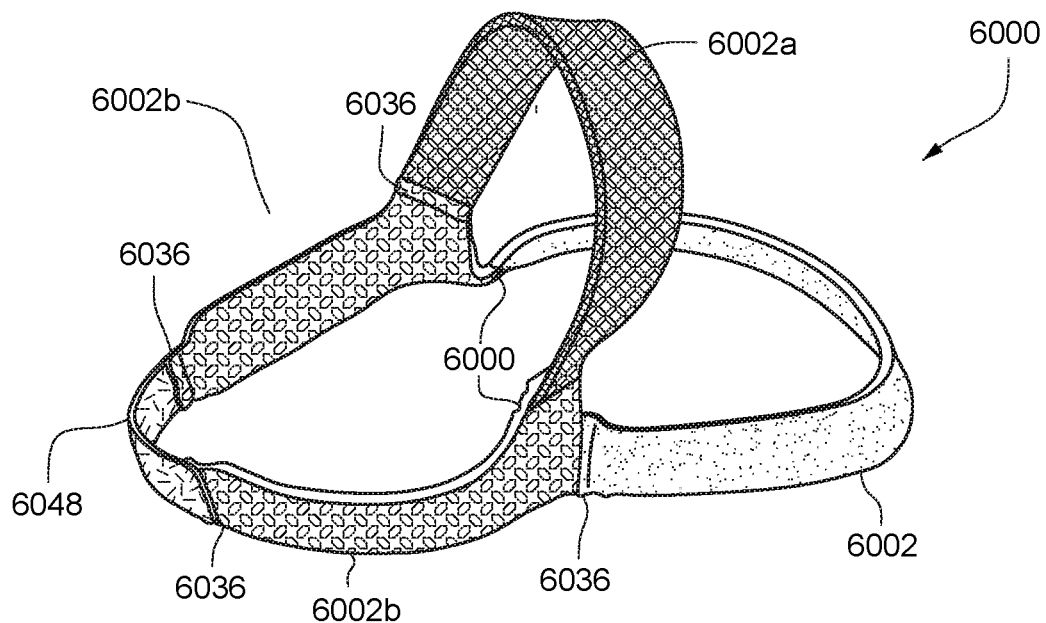

FIG. 4H shows headgear with structures omitted to view underlying structure.

Figure 4I:
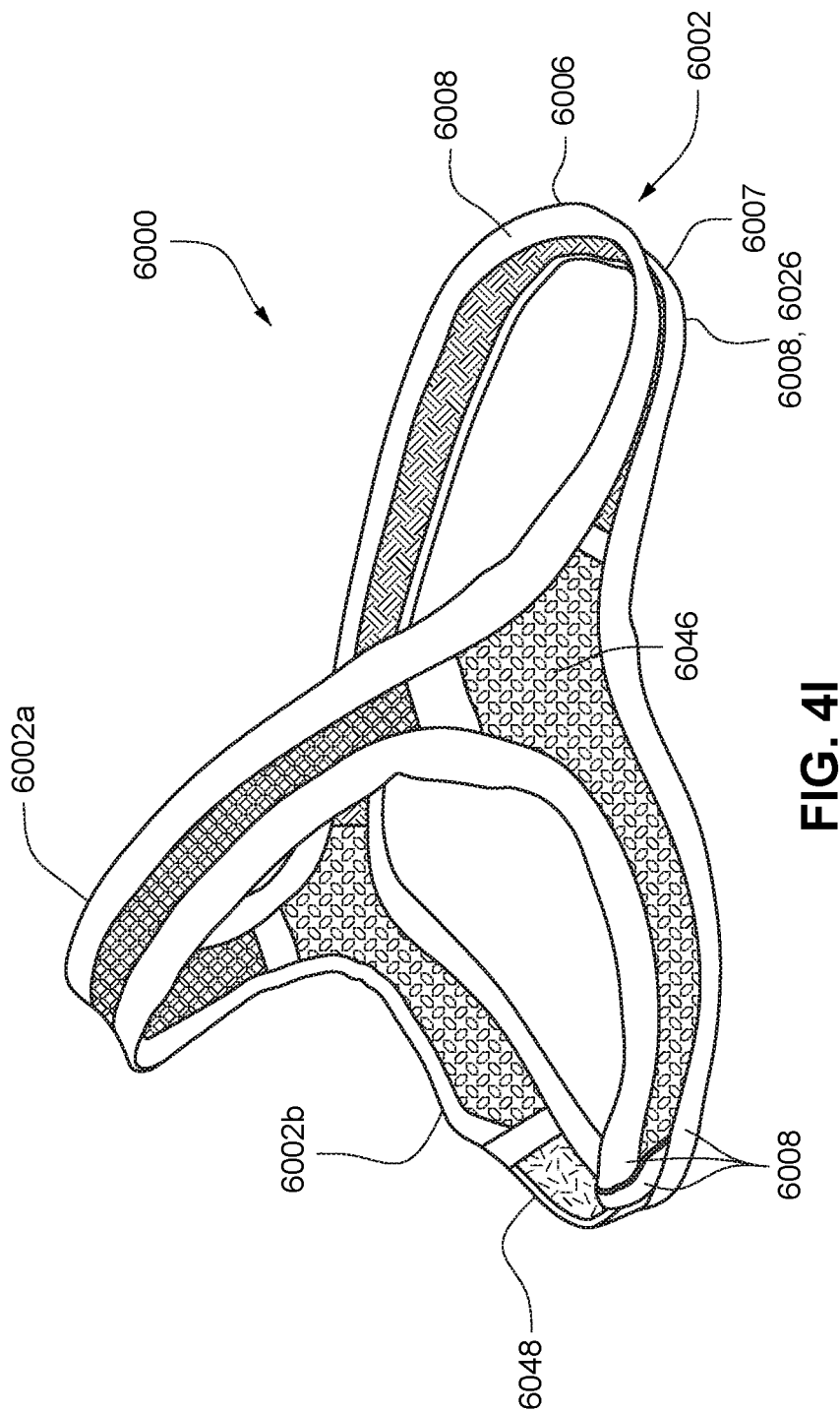

FIG. 4I shows headgear without a mask or connection to a mask.

Figure 4J:
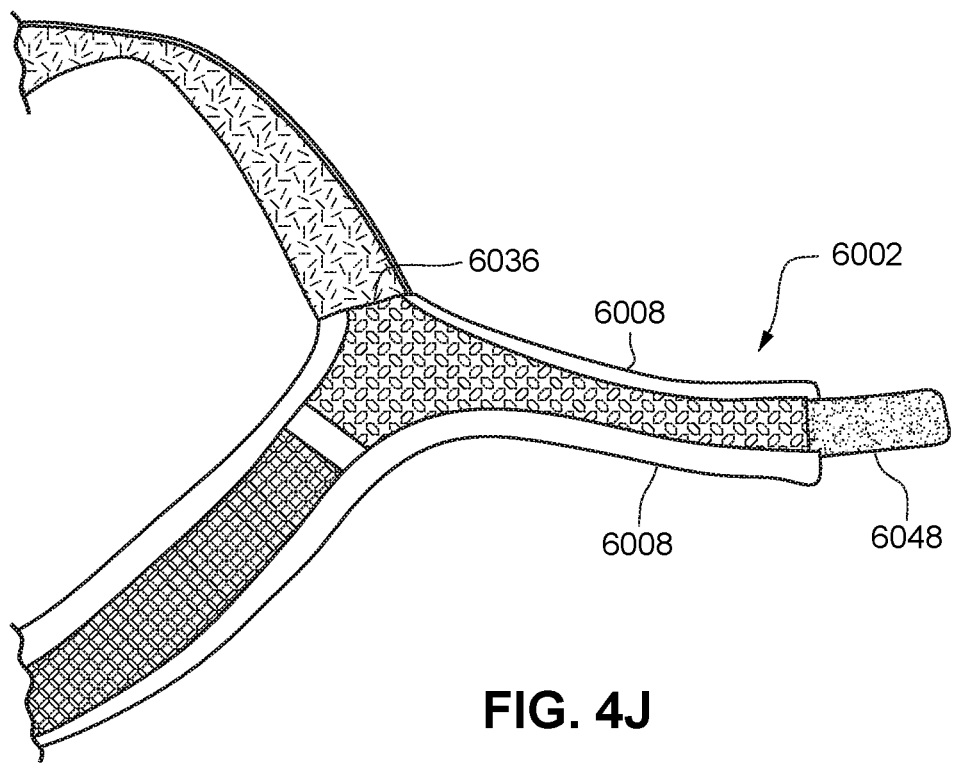

FIG. 4J shows a partial view of headgear where strap portions intersect.

Figure 4K:
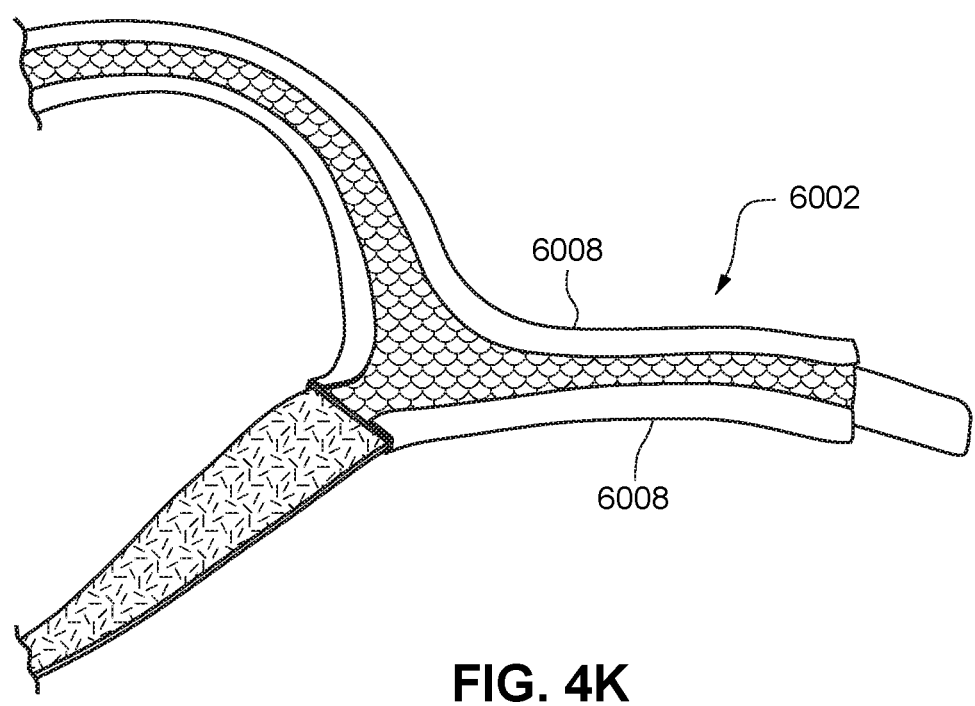

FIG. 4K shows the opposite side of the headgear illustrated in FIG. 4J.

Figure 4L:
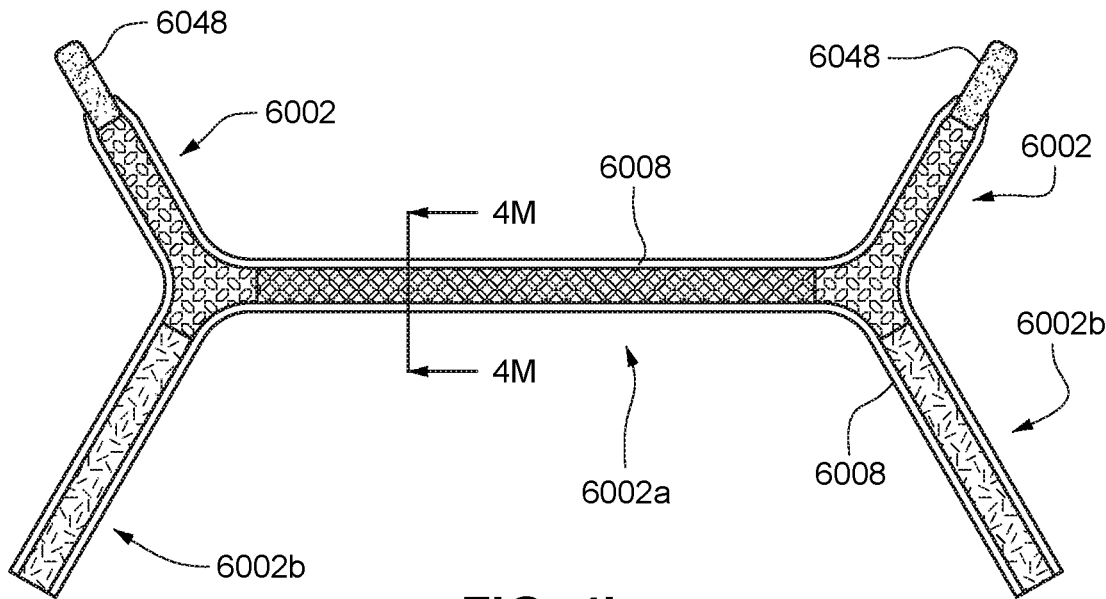

FIG. 4L shows partially completed headgear in a flat condition without a mask.

Figure 4M:
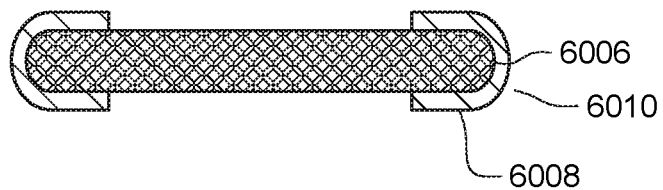

FIG. 4M shows a cross section taken through FIG. 4L.

Figure 4N:
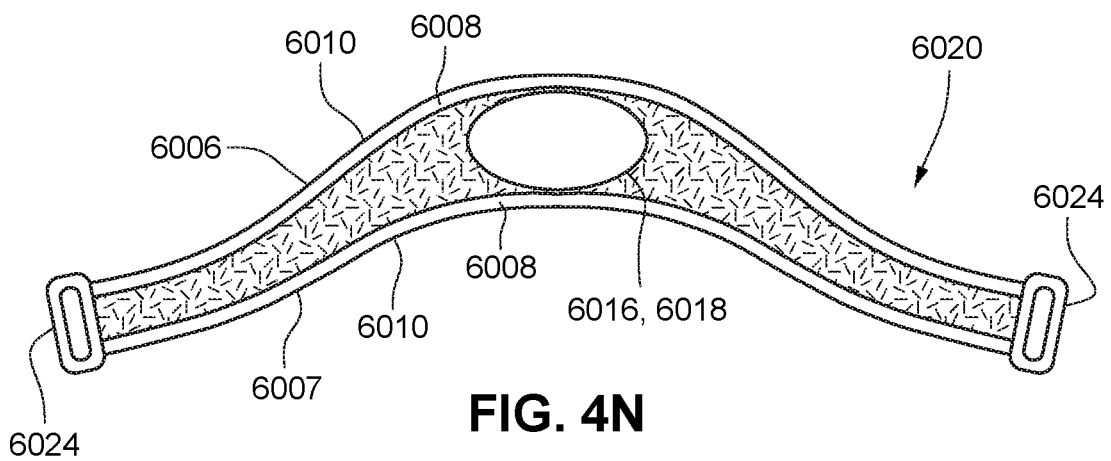

FIG. 4N shows a strap to retain a mask and attach to the headgear illustrated in FIG. 4L.

Figure 4O:
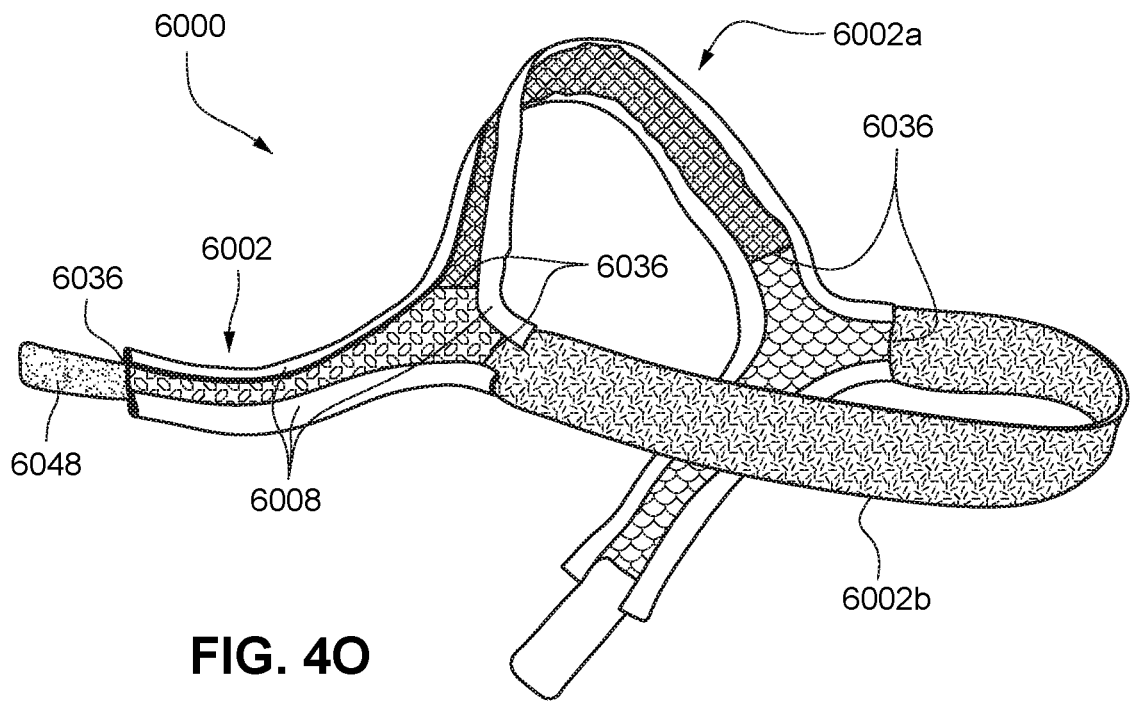

FIG. 4O shows headgear in an assembled condition but collapsed.

Figure 4P:
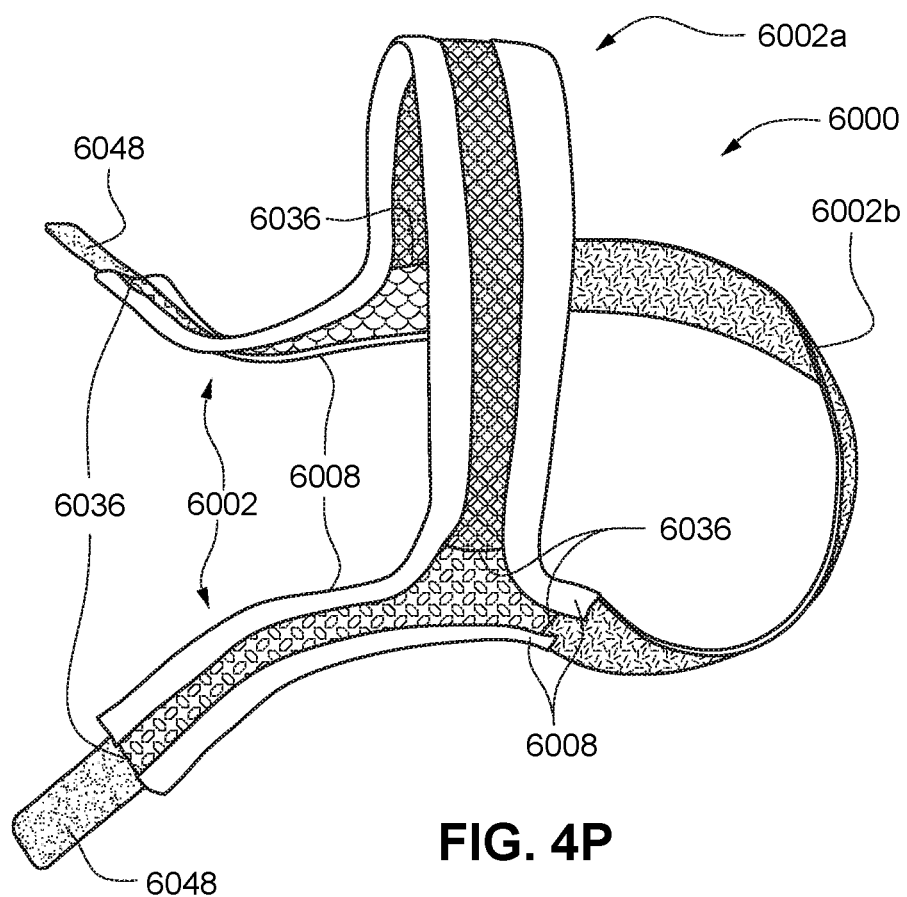

FIG. 4P shows headgear in an assembled condition.

Figure 4Q:
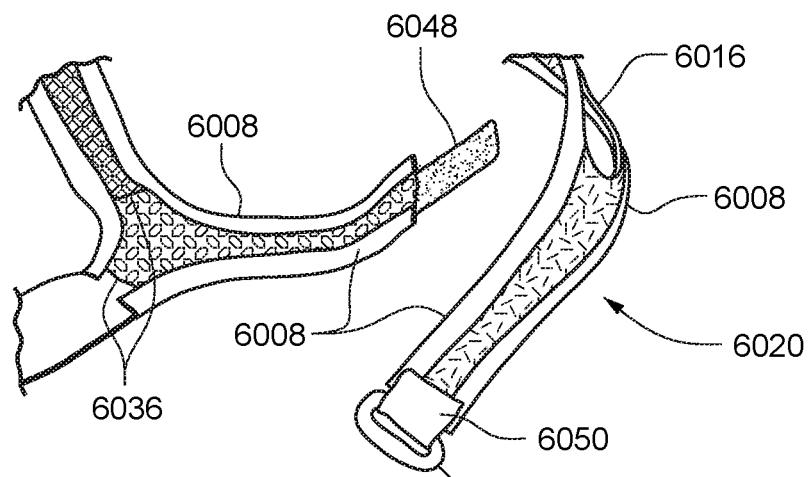

FIG. 4Q shows headgear with two strap portions disconnected from one another.

Figure 4R:
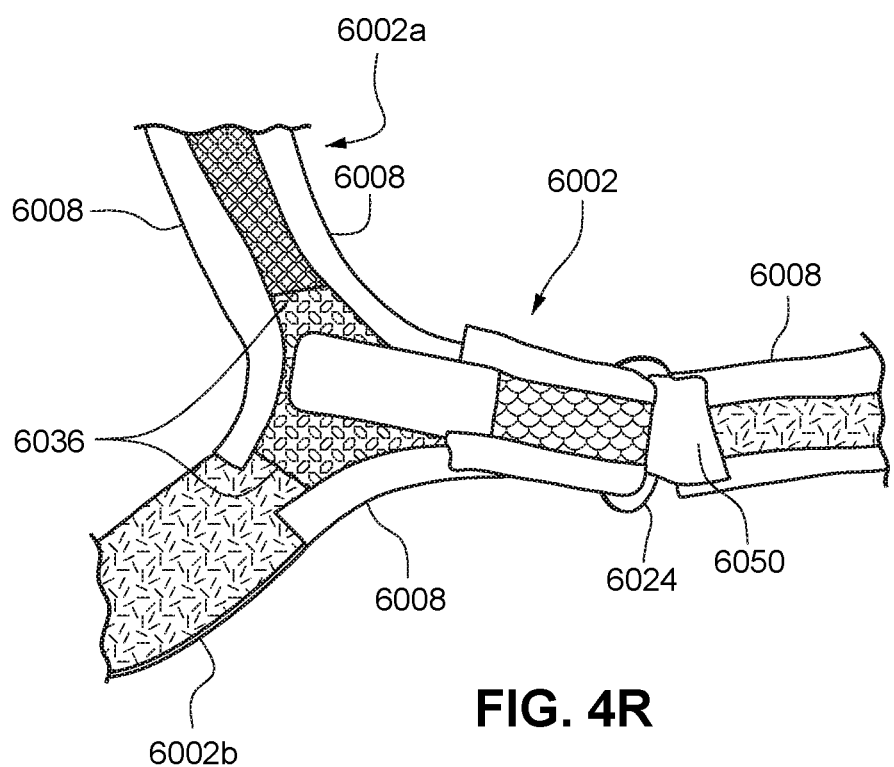

FIG. 4R shows the headgear of FIG. 4Q with the straps connected to one another.

Figure 4S:
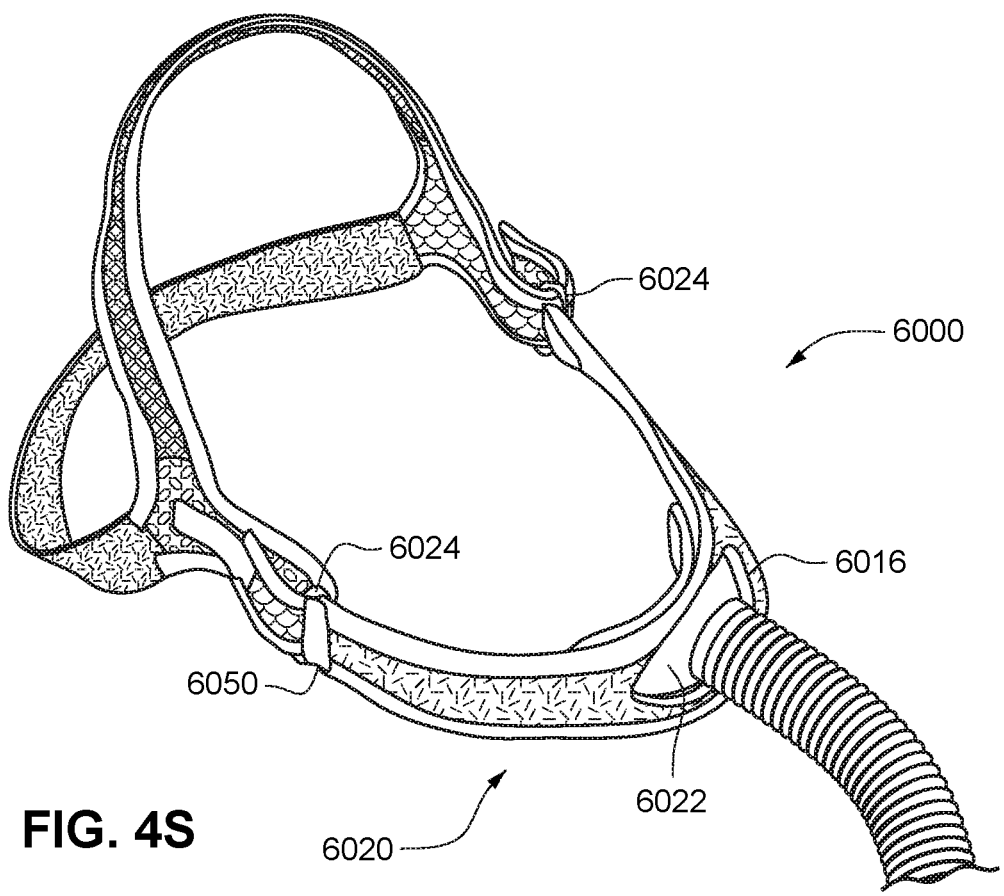

FIG. 4S shows the headgear of FIG. 4R with a mask.

Figure 4T:
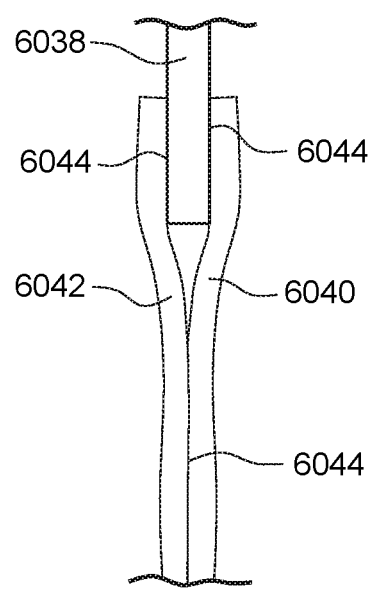

FIG. 4T shows a cross-section through a strap portion of headgear.

Figure 4U:
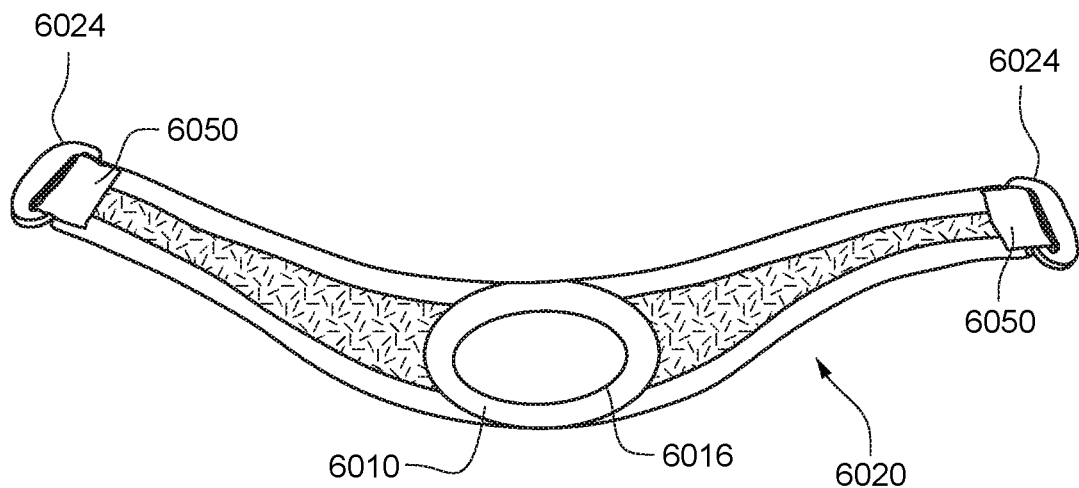

FIG. 4U shows a strap portion with an opening for a mask.

Figure 4V:
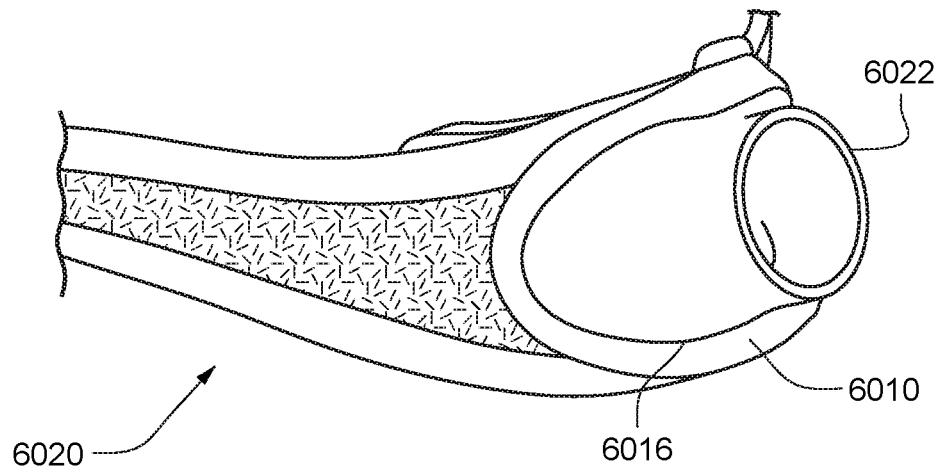

FIG. 4V shows the strap portion of FIG. 4U with a mask.

Figure 4W:
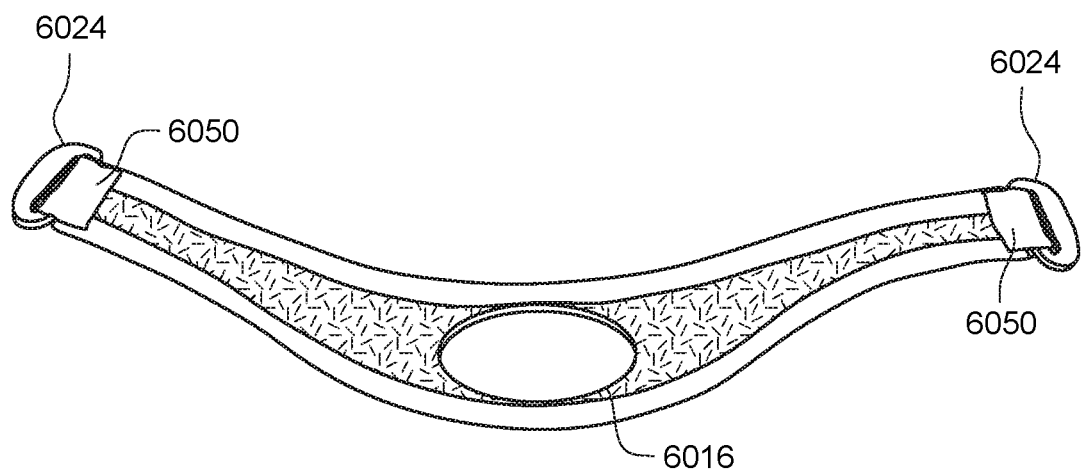

FIG. 4W shows a strap portion with an opening for a mask.

Figure 4X:
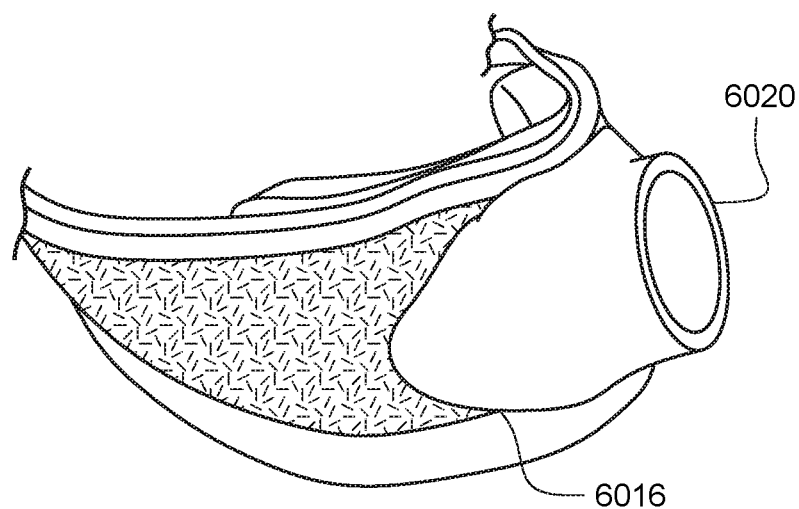

FIG. 4X shows the strap portion of FIG. 4W with a mask.

Figure 4Y:
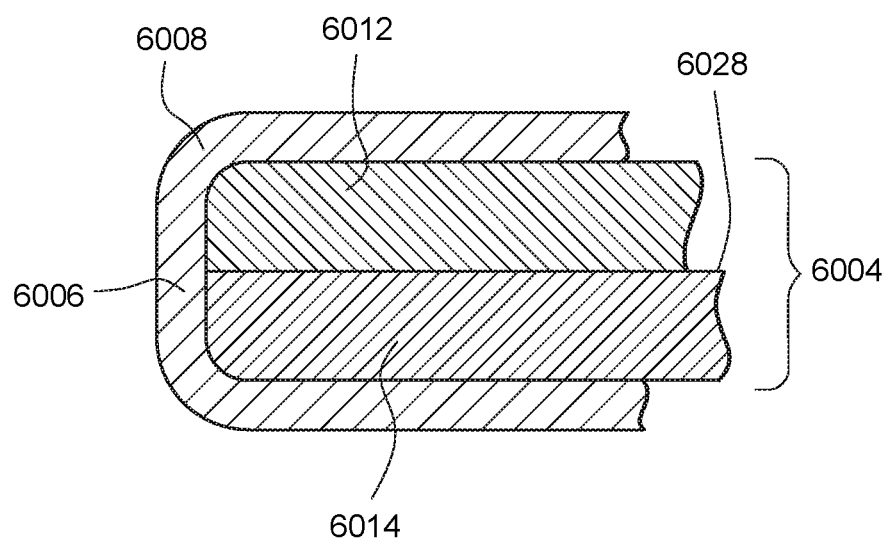
Figure 5A:
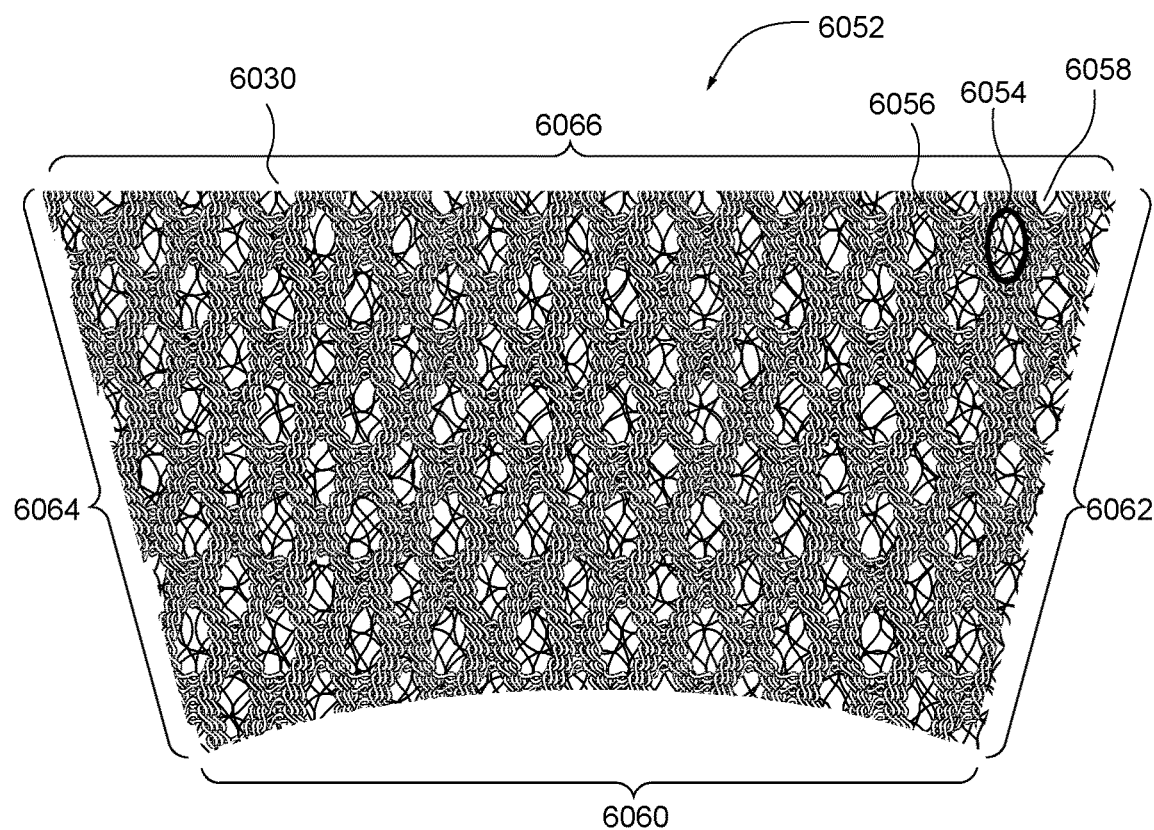

FIG. 4Y shows a strap portion with a layered structure according to an example of the disclosed technology.s FIG. 5A shows a part used in a headgear assembly.

Figure 5B:
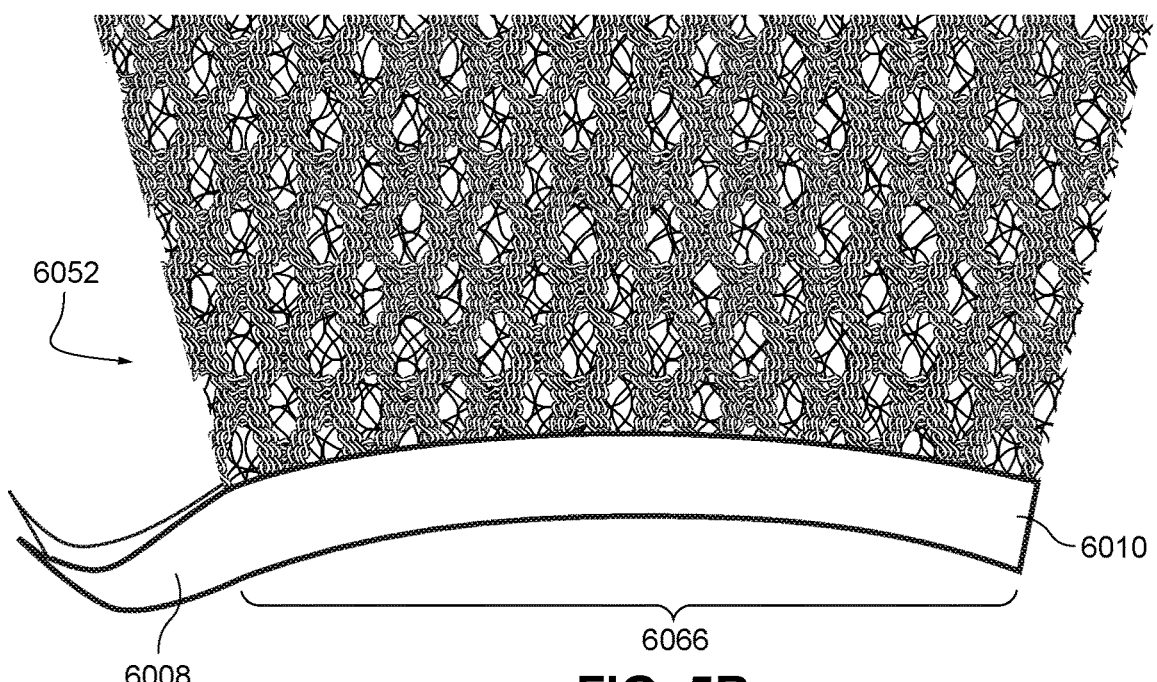

FIG. 5B shows the part of FIG. 5A with the addition of a component.

Figure 5C:
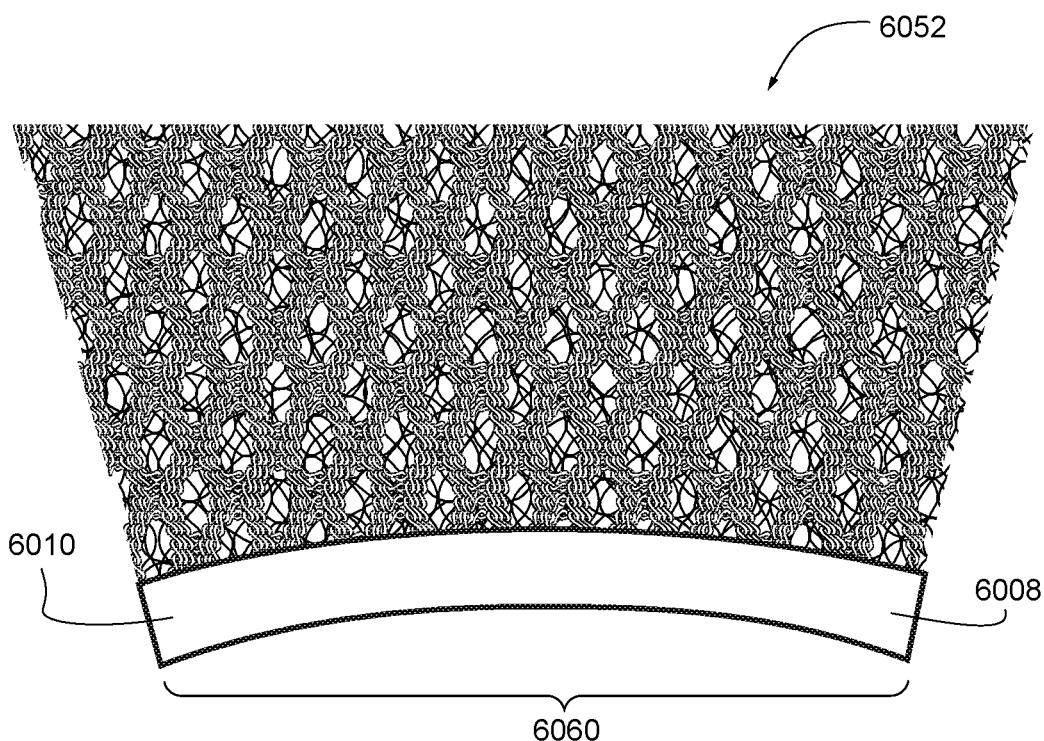

FIG. 5C shows the part of FIG. 5B with the additional component trimmed.

Figure 5D:
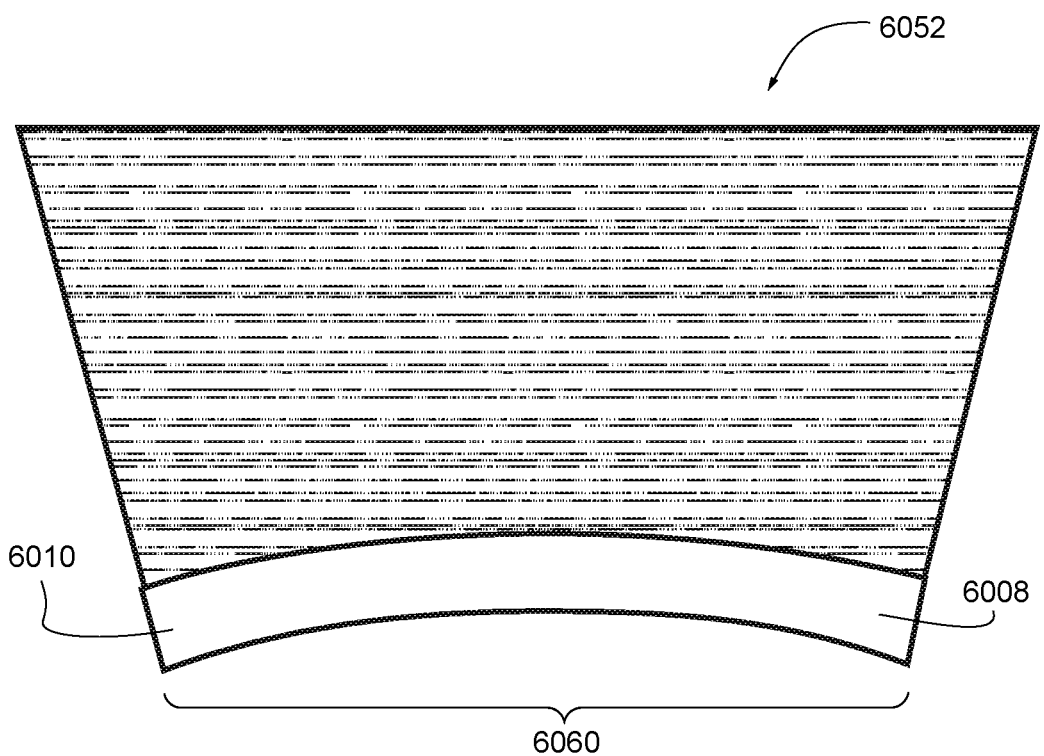

FIG. 5D shows the reverse side of the part in FIG. 5C.

Figure 5E:
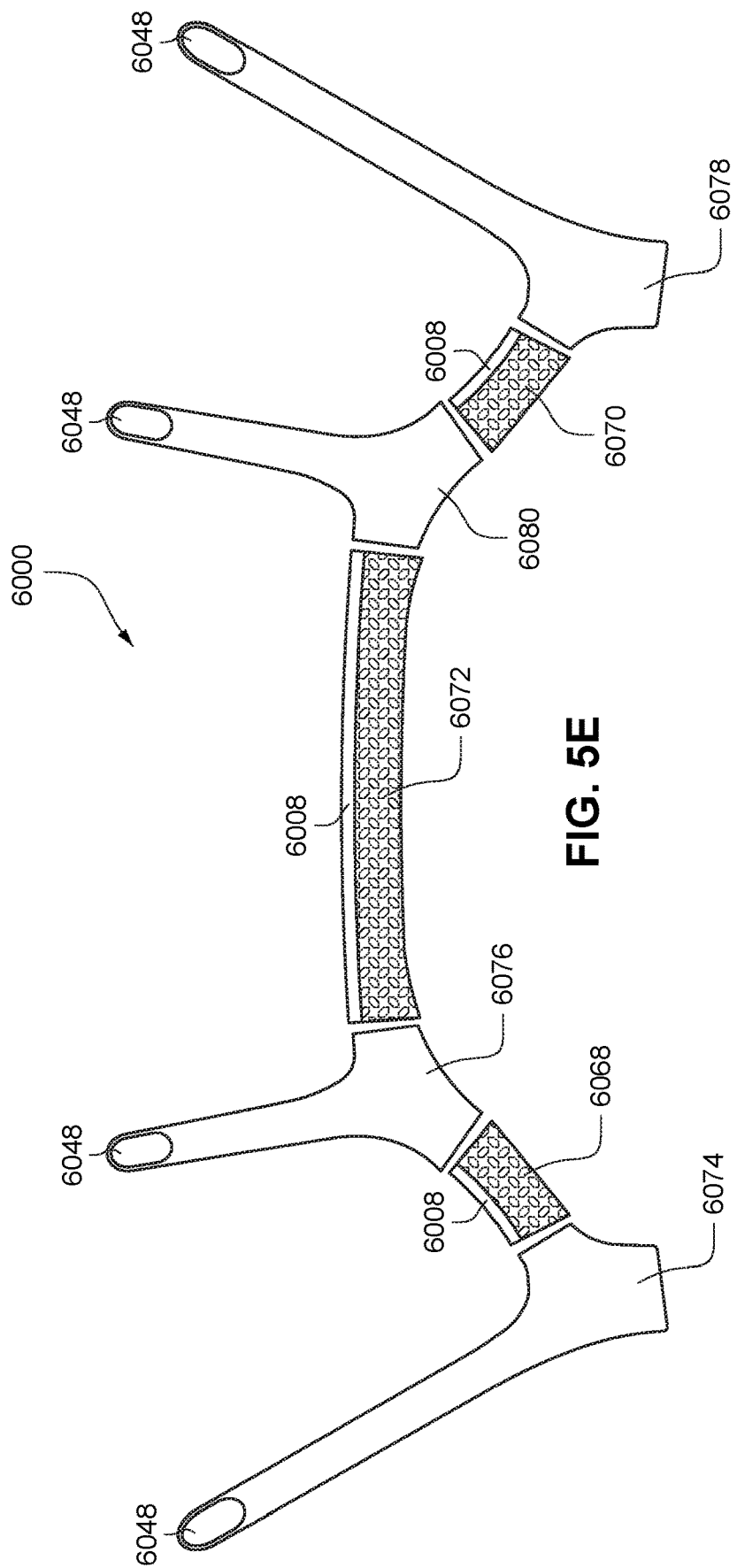

FIG. 5E shows a plurality of parts for a headgear assembly that are adjacent to one another prior to being joined together.

Figure 5F:
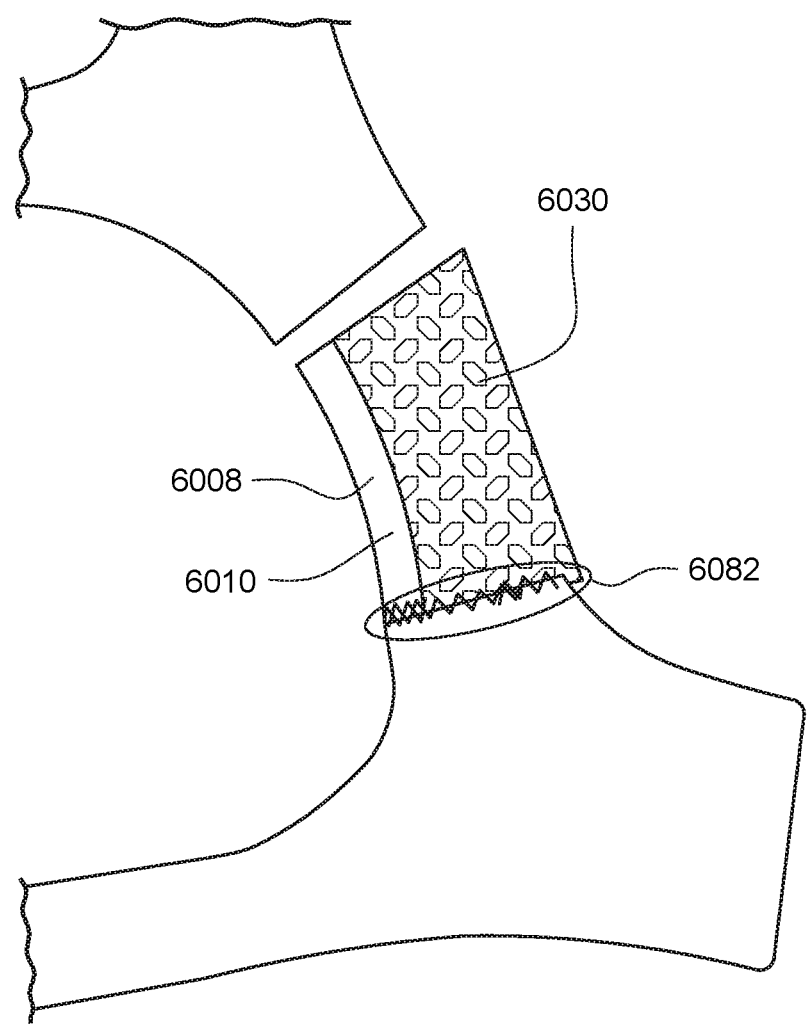

FIG. 5F shows three parts of the plurality of FIG. 5E with two of the parts joined and the third not joined.

Figure 5G:
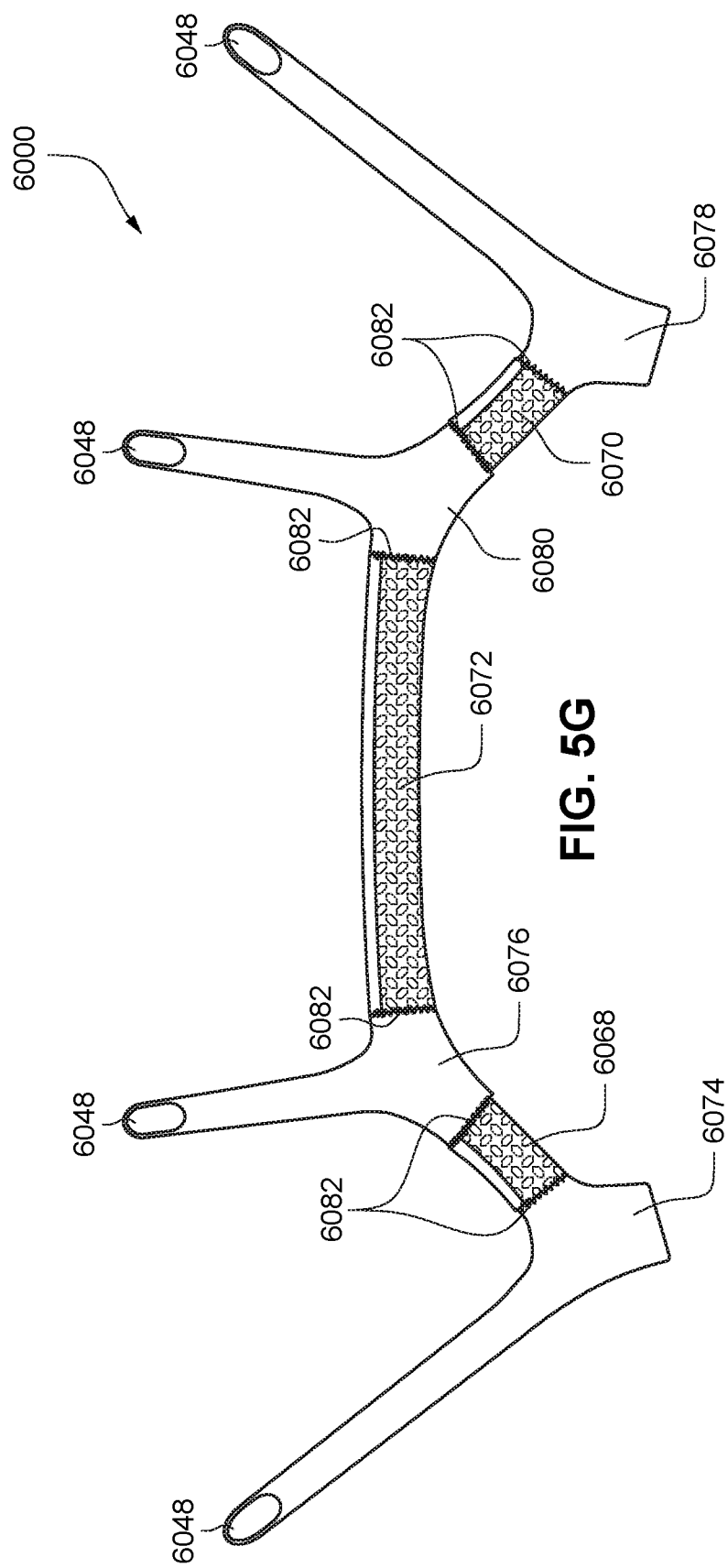

FIG. 5G shows all of the parts of FIG. 5E joined together in a flat configuration.

Figure 5H:
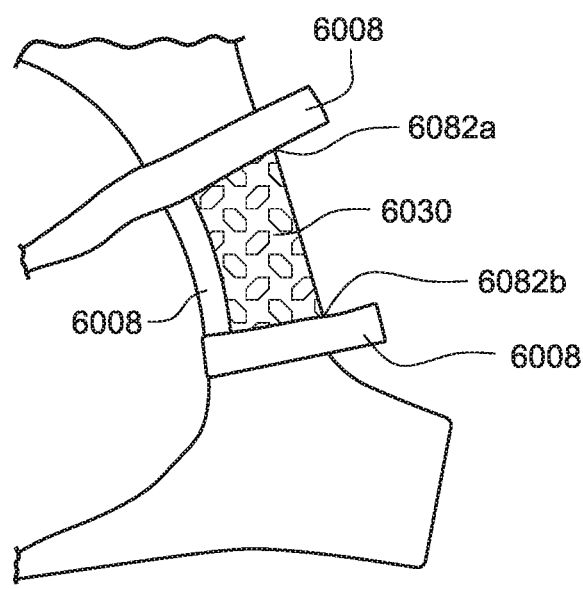

FIG. 5H shows application of a component over a joint and partial application over another joint.

Figure 5I:
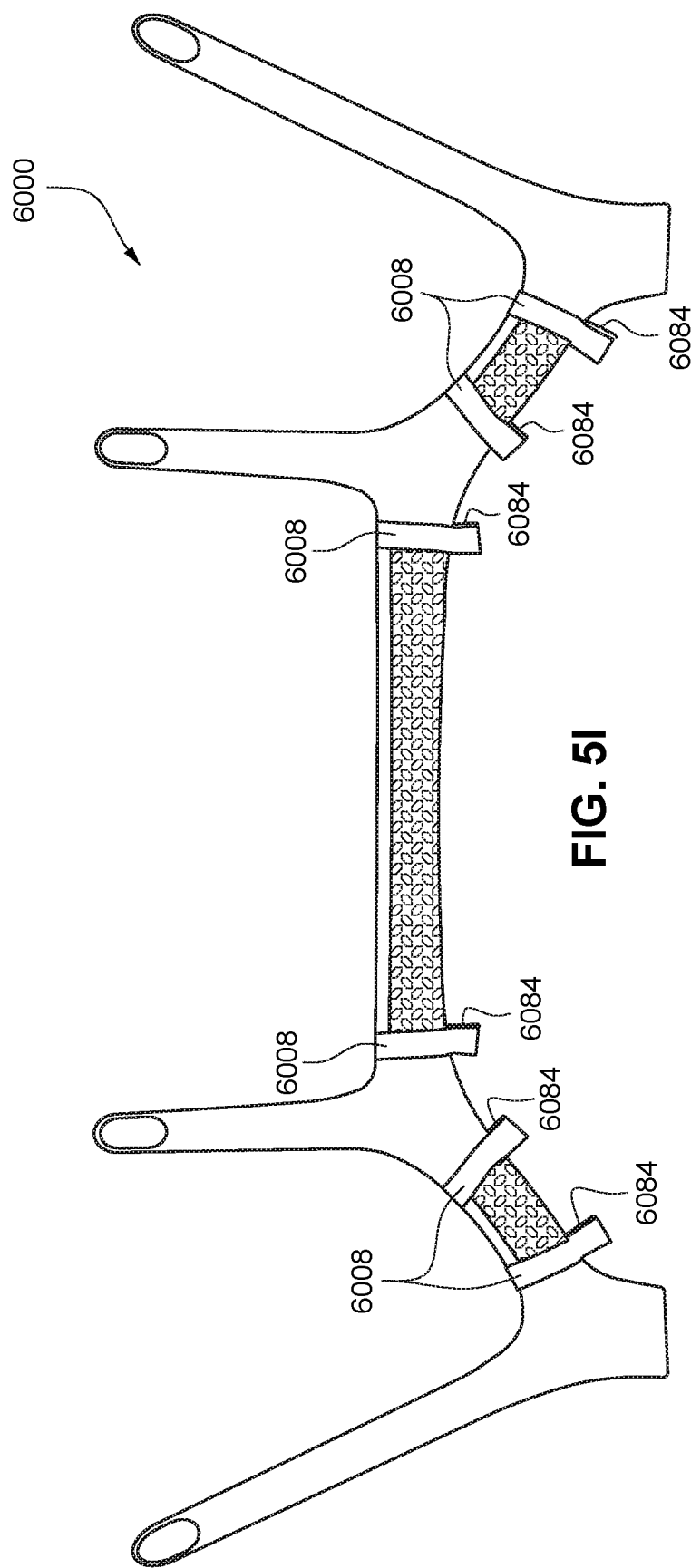

FIG. 5I shows application of the component over all joints in the flat condition.

FIG. 5J shows the component applied over all of the joints after trimming the component.

FIG. 5K shows the headgear after a joining process that changes the headgear from a flat to a non-flat configuration.

Figure 5L:
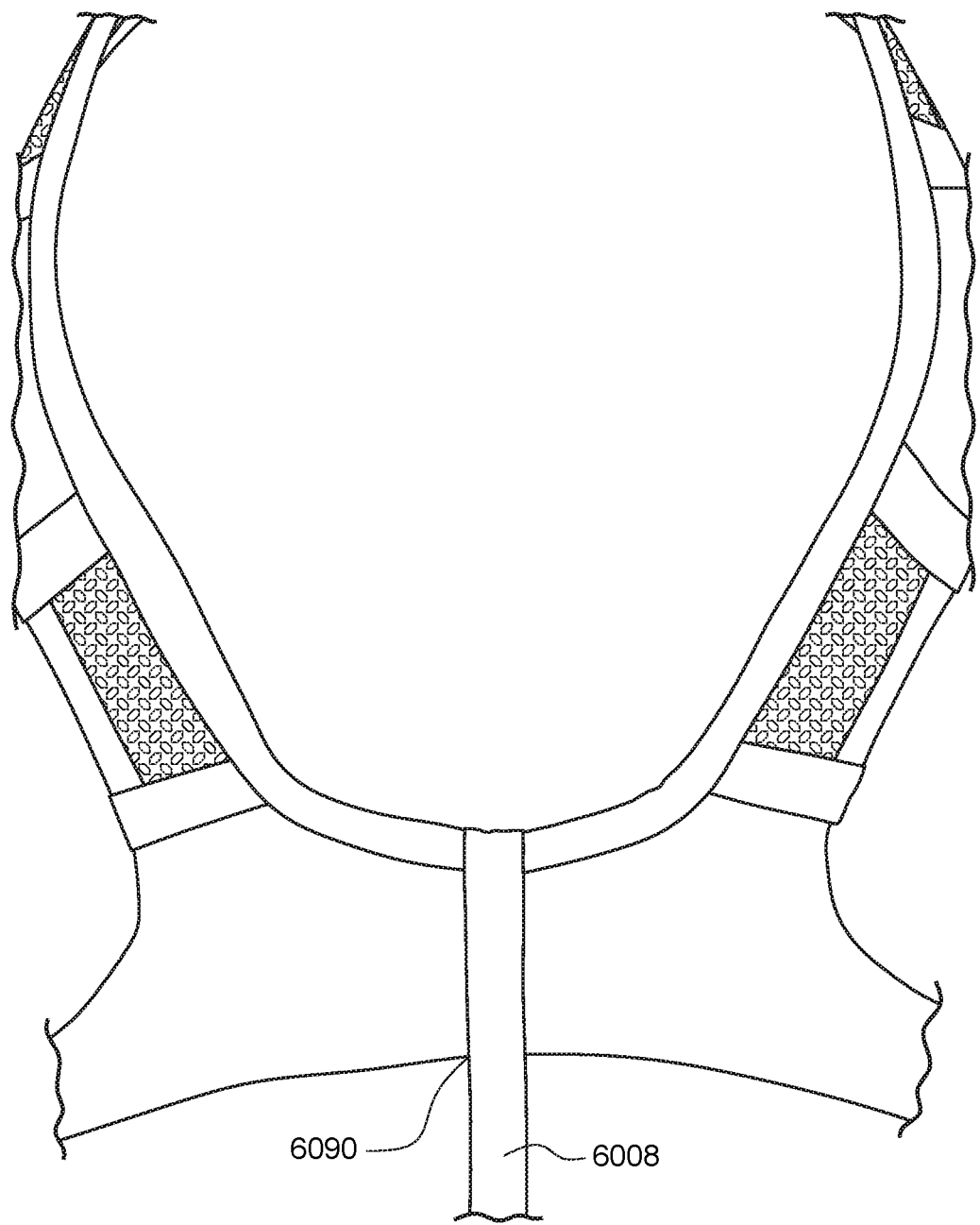

FIG. 5L shows a component applied over the joint of FIG. 5K.

Figure 5M:
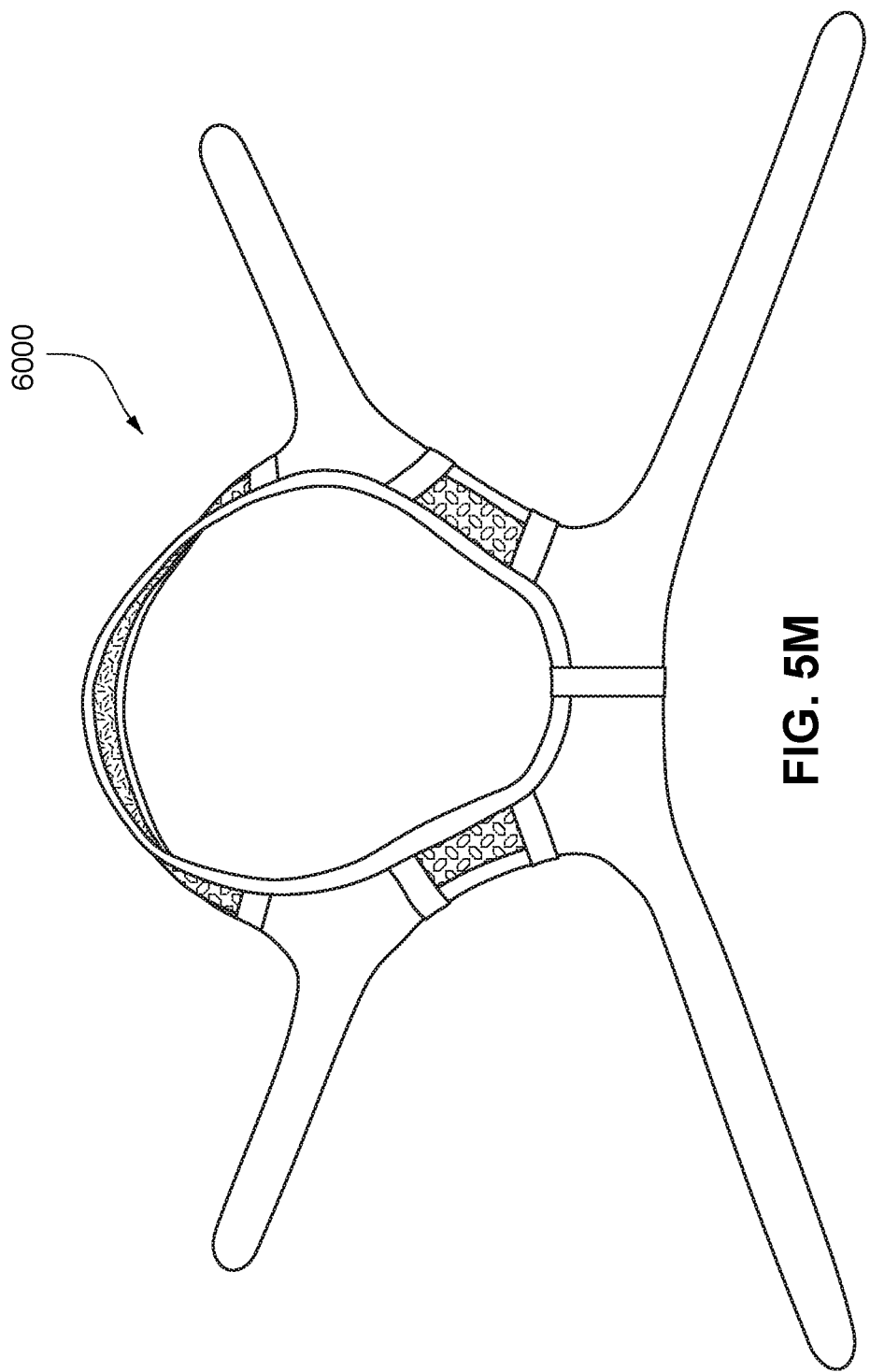

FIG. 5M shows the component of FIG. 5L after being trimmed.

Figure 5N:
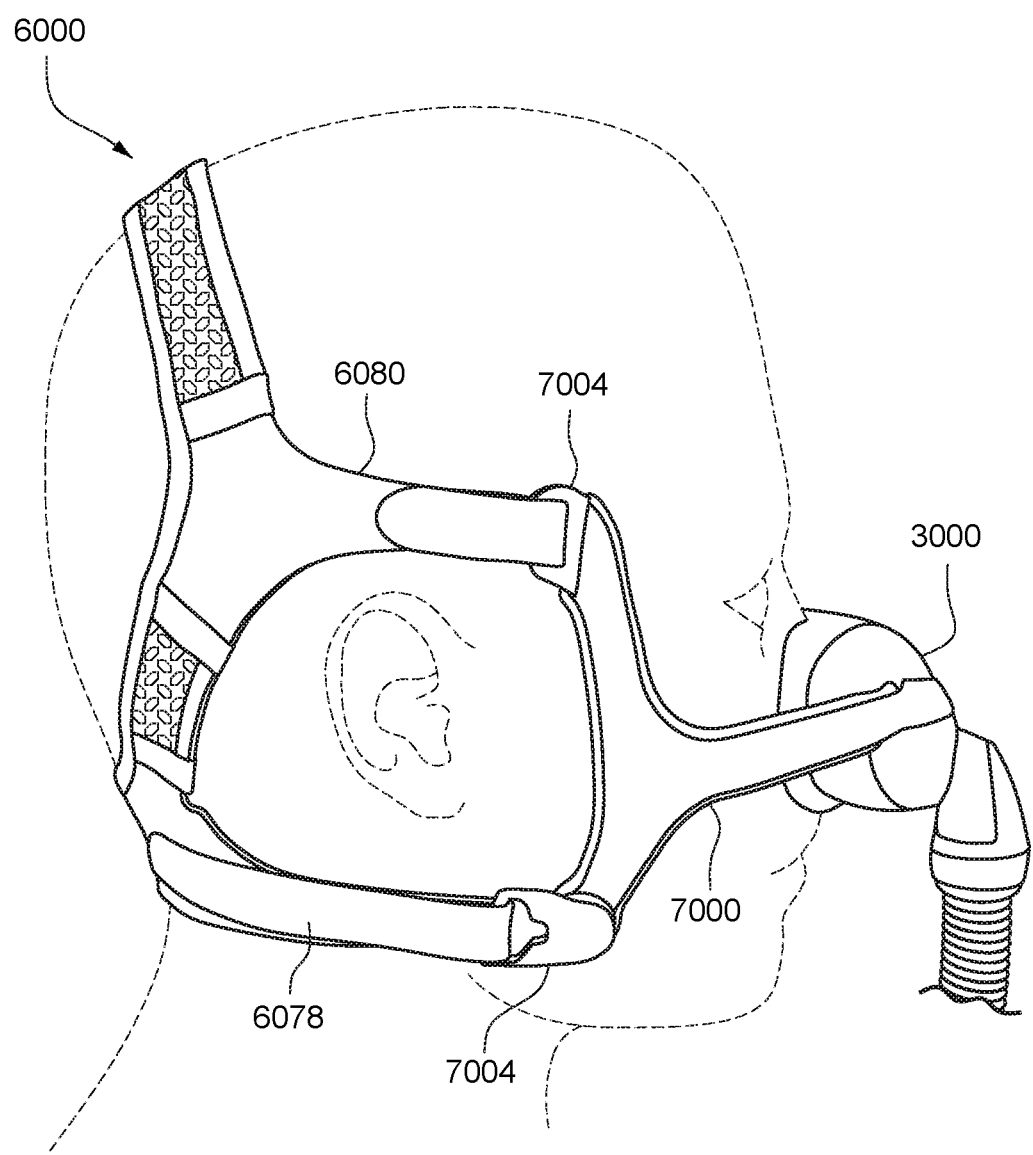

FIG. 5N shows completed headgear in use with a mask.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700.

In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200.

4.3.3 Positioning and Stabilising Structure

The seal-forming structure 3100 of the patient interface 3000 of the present technology may be held in sealing position in use by the positioning and stabilising structure 3300. As illustrated, the positioning and stabilising structure 3300 is in the form of headgear 6000.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

4.3.4 Vent

In one form, the patient interface 3000 includes a vent 3400 constructed and arranged to allow for the washout of exhaled gases, e.g. carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.5 Decoupling Structure(s)

In one form the patient interface 3000 includes at least one decoupling structure, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Ssphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.3.10 Headgear

The headgear 6000 illustrated throughout FIGS. 4A-4Y includes various patterns in the illustrations. Due to the limitations of black and white line drawings, the patterns, unless noted explicitly herein, are intended to allow the reader to distinguish between materials that may be similar and materials that may be different. Except as explicitly set forth herein, the patterns should not be considered limiting.

FIGS. 4A-4E illustrate headgear 6000 that includes straps, such as strap 6002, made of a first flexible material 6004. The strap 6002 extends generally from the area of a patient's Otobasion superior or Temporal bone to a breathing mask 6022. Another strap 6002a extends from the area of the patient's Otobasion superior or Temporal bone on one side of the patient's head, over the Parietal bone to the area of the patient's Otobasion superior or Temporal bone on the other side of the patient's head. Another strap 6002b extends from the area of a patient's Otobasion superior or Temporal bone on one side of the patient's head, wraps around the Occipital bone and/or Trapezius m. to the other side of the patient's head in the area of the patient's Otobasion superior or Temporal bone. As illustrated in these figures, the straps 6002a, 6002b form a continuous structure that conforms to and cradles the back and top of the patient's head. The continuous structure may be shaped similarly to a circle or ellipse so that the patient's head protrudes at least partially through the circle or ellipse. Except as expressly noted herein, the straps 6002a, 6002b may have the same or substantially the same structure as the strap 6002. Thus for the sake of brevity, only the strap 6002 will generally be referenced hereinafter.

The strap 6002 includes an elongate edge 6006 with a second flexible material 6008 wrapped around the elongate edge 6006. The second flexible material 6008 may be an elastic material. Preferably the second flexible material 6008 has a higher degree of elasticity than the first flexible material 6004. For example, the second flexible material may be similar to, or have properties similar to, that used in elastic bands for clothing. Also, the straps 6002a, 6002b may have a higher degree of elasticity than the strap 6002. A second elongate edge 6007 is opposite the elongate edge 6006 and together they define a width of the strap 6002. The second elongate edge 6007 may be substantially identical to the elongate edge 6006. Indeed, all elongate edges of the present technology may be formed in a similar manner. Thus the remainder of the present disclosure will only separately discuss other elongate edges where they differ from the elongate edge 6006.

The strap 6002a may comprise a mesh spacer fabric where holes may be visible. This configuration may be more visually aesthetic and may cause a user to perceive the headgear as lighter. This configuration may also be more breathable. It may be preferable to avoid mesh spacer fabric for the straps (e.g. strap 6002 and 6002b), because there may be a risk that those straps could snag and/or hook on bed linen due to the open nature of mesh spacer fabric open nature. Using mesh spacer fabric on a crown strap (e.g., strap 6002a) may not experience this problem because the top of the head typically does not contact bed linen and/or a pillow when the patient is sleeping.

The second flexible material 6008 is wrapped around the elongate edge 6006 to form a V-shaped fold 6010. As discussed herein, a V-shaped fold is intended to describe the process for creating the fold, which may not necessarily reflect the final shape of the fold. For example, as illustrated in FIG. 4M, the V-shaped fold 6010 conforms to the underlying material, which has a rounded edge, and results in a configuration that may be closer to a U-shape when viewed in cross-section. If the underlying material is relatively thinner or has a pronounced edge, the final shape of the V-shaped fold may be closer to a V-shape than what is illustrated in FIG. 4M. The V-shaped fold 6010 may enable a continuous edge all around the headgear 6000 or a continuous edge in any sub-portion of the headgear 6000. The V-shaped fold 6010 may be very visually appealing, as well as being smooth to avoid snagging or bumps in certain spots compared to if the edging material is made of multiple sections.

The second flexible material 6008 may be applied with the V-shaped fold 6010 with the aid of a Macpi machine model number 335 32, which can be used to apply a strip of adhesive along the edge of fabric. Macpi machine model number 335 48 may be used to fold over and apply the second flexible material 6008. In this way, adhesive may fix the second flexible material 6008 to the strap 6002 with the V-shaped fold 6010 by applying adhesive on opposite surfaces of the strap 6002 near the elongate edge 6006 and affixing the second flexible material 6008.

The material used for the V-shaped fold 6010 may be supplied with or without a pre-laminated adhesive. If a pre-laminated adhesive is not used, the MACPI machine may be used to laminate adhesive on, where the process and/or material can be controlled to suit the particular strap material. In the same process, after the lamination, the second flexible material 6008 may be bonded to the strap material (e.g. spacer fabric or Breath-O-Prene®). Breath-O-Prene® strap portions may be connected together, for example, by ultrasonic welding, stitching or any other suitable means. Attaching spacer fabric strap portions together may be achieved, for example, using stitching.

The second flexible material 6008 may extend along and cover an entire width of the strap 6002. For example, in FIG. 4A, the side of the strap 6002 that faces the patient may be completely covered by the second flexible material 6008 such that the second flexible material 6008 extends to and is wrapped around the second elongate edge 6007 in substantially the same manner as the elongate edge 6006. Alternatively, as illustrated in FIG. 4I, the second flexible material 6008 may not extend across the width of the strap 6002 and thus the second flexible material 6008 may be two separate pieces. This configuration may allow for an alternative second flexible material 6026 in place of the second flexible material 6008 so that the alternative second flexible material 6026 may have different properties, if necessary or desirable. For example, the alternative second flexible material 6026 could be an elastic with different extensive properties than an elastic used for the second flexible material 6008. The configurations in FIGS. 4A and 4I share a common feature in that on at least one side of the strap 6002, the second flexible material does not extend across the entire width of the strap 6002.

As illustrated in FIG. 4Y, the first flexible material 6004 may be formed of layers of material. For example, the first flexible material may include a third flexible material 6012 and a fourth flexible material 6014 that are adhered together by stitching, a layer of adhesive, ultrasonic welding or any other suitable substance or process for adhering the layers together. An adhesive film 6028 is illustrated. Although only two layers are illustrated, any number of layers may be provided. For example, three, four, or more layers may be provided, where the number of layers may be determined, for example, based upon the combined characteristics of the individual layers. As illustrated, the second flexible material 6008 may be wrapped around the layers of material such that edges of the material, and thus the stacked nature of the materials, is covered. If the second flexible material 6008 is sufficiently opaque, the stacked nature may not be visible when viewed along the elongate edge 6006.

The first flexible material 6004 may be any flexible material such as foam or a woven material. The woven material may be spacer fabric or other types of fabric or textile. A spacer fabric can be defined as a textile having an upper ground structure or layer, a lower ground structure or layer, and a floating or traversing yarn woven between the upper ground structure and lower ground structure to form a matrix like textile. The upper ground structure and lower ground structure may be formed from a fabric. The upper ground structure may have different properties than the lower ground structure, for example they may have different stretch, stiffness, flexibility, hand feel, or other characteristics. The upper and lower ground structures may be substantially parallel to one another. Spacer fabrics may be formed by flat knitting. At least one side (i.e. upper or lower ground structure) may be formed from a fabric having yarn of, for example, about 30-100 denier, 20-300 denier, or 50-200 denier for a pleasant hand feel. U.S. Patent Application Publication Nos. 2014/0102456 and 2014/0158136, both of which are incorporated by in their entireties, discuss spacer fabrics and some potential uses with respect to headgear. The first flexible material 6004 may also be Breath-O-Prene®, which may be easier to ultrasonically cut or die cut than spacer material.

FIGS. 4M and 4Y illustrate the elongate edge 6006 as rounded. A rounded edge may be formed by way of ultrasonic cutting. Alternatively, the elongate edge 6006 could be formed by other methods such as die cutting, which may result in a less-rounded cut or even a perpendicular intersection between the adjacent surfaces.

As best viewed in FIG. 4E, the strap 6002 transitions from the first flexible material 6004 to another flexible material, which is illustrated as a mesh material 6030. However, any flexible material, such as fabric or foam or layers thereof, may be used. Thus a first flexible strap portion 6032 of the strap 6002 includes the first flexible material 6004 and a second flexible strap portion 6034 of the strap 6002 includes the mesh material 6030. Where the first flexible strap portion 6032 joins the second flexible strap portion 6034, the intersection 6036 is covered by the second flexible material 6008. The second flexible material extends along the first and second elongate edges 6006, 6007 as well as the intersection 6036 between strap portions. Thus a portion of the second flexible material 6008 extends along a short edge transverse to the elongate edge 6006 defined at the intersection 6036. The intersection 6036 is best viewed in FIG. 4H. A different material may also be used to cover the intersection 6036 if desired or the intersection may remain uncovered. See, e.g., FIG. 4J. At the intersection 6036, materials may be joined by any suitable and/or convenient method. Two examples are zig-zag sewing (a type of stitching) and ultrasonic welding. Another example of the way that materials may be joined together is discussed below with respect to FIG. 4T.

By including a first flexible strap portion 6032 and a second flexible strap portion 6034 made from different materials, the properties of the headgear 6000 may be controlled. For example, one portion may stretch relatively more than another. This may be beneficial based upon relative movement of anatomy near the different portions of the headgear 6000. In FIG. 4E, the first strap portion 6032 is adjacent the patient's jaw, which may move relative to the patient's skull whereas the second strap portion 6034 is located near a portion of the patient's skull that may not move. Thus the first strap portion 6032 may be allowed to stretch in use to accommodate patient movement. Also, different amounts of stretch may be useful when the patient puts on or takes off the headgear 6000. These and other aspects of the headgear 6000 may thus be optimized by using different flexible materials and joining them. One or both of the first flexible strap portion 6032 and the second flexible strap portion 6034 may be made from spacer fabric but with the properties thereof (such as the weave or fibre used) selected to provide a desired amount of elasticity such that the spacer fabrics are functionally different. Spacer fabric or other fabrics may be employed that provide elasticity or substantially no elasticity. Thus either strap portion could be elastic or substantially non-elastic.

FIG. 4F illustrates the headgear 6000 in a flat condition prior to being fully assembled. This illustrates that the headgear 6000 may be formed flat and that after assembly the headgear may fit to the complex shape of the patient's head. In FIG. 4F, the straps 6002b (top and bottom in the figure) may have their free ends connected together and the straps 6002 may have their free ends connected to a breathing mask 6022 to result in the configuration illustrated in FIGS. 4A-4E. With this configuration, various strap materials for different strap portions may be joined together. The second flexible material 6008 may be one continuous and/or uninterrupted piece (e.g., cut from a single sheet) and then applied to the patient-side (i.e., the bottom side or side not visible in FIG. 4f) of the headgear 6000 and then wrapped around the elongate edge 6002. An adhesive sheet may be used to attach the second flexible material 6008. The adhesive sheet could be cut from a single sheet of adhesive (similar to that described above for the flexible material 6008) or could be cut into different components. This option may be beneficial if, for example, different types of adhesive are better suited for different areas of the headgear. For example, different types of adhesive may be better suited for joining the second flexible material 6008 to the different strap materials. Different types of adhesive may be desirable in areas where the headgear is likely to experience different levels of stretching in use. Other types of adhesive, such as adhesive applied in liquid (e.g., brushed on or sprayed on adhesive) may also be desirable to achieve different adhesive or assembly requirements.

FIG. 4G illustrates the headgear of FIG. 4F but in a non-flat condition with part of the side facing the patient visible.

FIG. 4T illustrates one way in which strap portions may be joined together. A first layer 6038 of one strap portion may be inserted between a second layer 6040 and third layer 6042 of a second strap portion. The second layer 6040 and the third layer 6042 may be connected by a layer of adhesive 6044, or any other suitable joining process, that does not extend to the ends of the second layer 6040 and third layer 6042. The layer of adhesive 6044 may be the same as or different from the adhesive film 6028. The resulting strap structure is substantially Y-shaped when viewed along the elongate edge 6006. The first layer 6038 may then be inserted into the Y-shape and secured between the second layer 6040 and third layer 6042 with additional layers of the adhesive 6044, or any other suitable joining process. This type of joining technique may be applied where three legs come together to form a Y-shaped profile 6046 when viewed from the patient's side (e.g., when viewed from a width side of the strap) as illustrated, for example, in FIGS. 4E and 4I.

The second layer 6040 and third layer 6042 may advantageously have different properties. For example, one of the second layer 6040 and the third layer 6042 may be half of a hook and loop fastener, such has the loop half. The first layer 6038 may be the other half of a hook and loop fastener, such as the hook half. This configuration would allow the strap to have a configuration allowing the strap to connect to itself as illustrated, for example, in FIG. 4S.

FIGS. 4J and 4K illustrate how a construction with different layers may result in a patient-side (e.g., FIG. 4K) of headgear versus and exterior side (e.g., FIG. 4J) of headgear with distinct materials and/or material intersections. Not including any intersections with the second material 6008, the four patterns of FIG. 4J illustrate four different intersections whereas the three patterns of FIG. 4K illustrate only two intersections. The result may or may not be as visually distinct as illustrated in the figures, which will depend on the visual differences, if any, of the materials chosen.

FIGS. 4O and 4P are similar to FIGS. 4J and 4K in that different materials intersect and have different configurations on the patient side versus the outside. However, FIGS. 4O and 4P differ in that the same number of intersections are present on the patient side and the outside of the headgear even though different materials are used in portions of the patient side versus portions of the outside of the headgear. In these figures, the strap 6002b may be an elastic material.

Another benefit of a two-layered structure is that a side of a strap facing a patient may have different properties than a side facing away from a patient. For example, the side of a strap facing a patient may preferably have a soft touch or feel to avoid irritation. A flexible material may not have such properties while providing adequate structural integrity for use in headgear. Alternatively, if a flexible material has adequate structural integrity as well as appropriately soft touch and feel but the flexible material may not be well suited for connecting to the hooks of a hook and loop fastener (e.g., the surface does not include unbroken loops). If so, the loop half of the hook and loop fastener can be attached as an outside layer. Or a fabric that has unbroken loops can be applied.

FIG. 4L is similar to FIG. 4I except that the straps 6002 are substantially straight in the flat condition and may employ the two-layered structure discussed above. The straps 6002 may include hook material 6048 so that the strap can fold back and attach to the material adjacent to the hook material 6048.

FIGS. 4H and 4I illustrate two stages of assembly for headgear 6000. In FIG. 4H, various straps are attached together to form the basic shape of the headgear. The various straps and strap portions may be formed of different materials as indicated by the different patterns used in FIG. 4H. FIG. 4H differs from FIG. 4I most notably by the omission of the second flexible material 6008 and thus may illustrate an early stage of assembly versus FIG. 4I, which illustrates the second flexible material 6008 in place along the various edges.

Two notable differences in the configuration of the headgear 6000 in FIGS. 4H and 4I should be highlighted. First, there is no connection illustrated for a breathing mask. A hole 6018 as illustrated, for example, in FIGS. 4N and 4U could be provided in strap 6002 but has been omitted for clarity of these figures. Second, an elastic strap 6048 is illustrated between and connecting the ends of the straps 6002b. Such an elastic strap 6048 may be included in any of the headgear illustrated in this disclosure. The elastic strap 6048 may provide benefits such as greater adjustability or level of comfort for patients of varying head size while providing only one size of headgear. And the elastic strap 6048 may allow for the omission of, or reduction of, other relatively complex adjusting arrangements such as buckles or other fasteners. Omission of such buckles or fasteners may be beneficial in areas of the headgear where straps do not need to be disassembled during normal use but adjustment may be required.

FIGS. 4A, 4B, 4D, 4E, 4N, 4Q, 4S and 4U-4X illustrate a connection 6016 for a breathing mask 6022. In FIGS. 4N, 4Q, 4S and 4U-4X, the connection 6016 is illustrated in the form of a hole 6018 through a strap 6020, where the hole 6018 may be sized to conform to an outer perimeter of a section of the breathing mask 6022 such that the breathing mask 6022 at least partially passes or protrudes through the strap 6020. The strap 6020 may be similar to the strap 6002 in that two elongate edges 6006, 6007 are provided where each may be covered with a V-shaped fold 6010 of the second flexible material 6008. Alternatively, the V-shaped fold 6010 may be made from a different material. The hole 6018 may be provided with a V-shaped fold 6010 (see, e.g., FIGS. 4U and 4V), or the V-shaped fold may be omitted (see, e.g., FIGS. 4N, 4Q, 4S, 4W and 4X). On opposed ends of the strap 6020, loops 6024 may be provided to allow another strap to pass there through. See, e.g., FIGS. 4Q-4S. The loops 6024 may be used in conjunction with a strap that can connect to itself as illustrated in FIG. 4S so that two different straps of the headgear 6000 can be connected together. This arrangement may allow a "set and forget" arrangement so the user does not have to adjust length after the initial set up. The user can don/doff the mask by simply sliding off and on as the headgear, preferably when the headgear is elastic.

The strap 6002 and the strap 6020 may have a width of 16 mm to 24 mm or any value in between. For example, the width may be about 20 mm. If the strap width is too narrow it will pierce the skin, i.e. leave marks. Also, if it is too narrow, the geometry may be more likely to allow the strap to crease, kink and/or fold over. A certain level of width may provide rigidity of the side strap via geometry. If the strap width is too wide, then there is likely to be more physical contact with the user's face which may be uncomfortable and increased width will increase weight.

The loops 6024 may be attached to the strap 6020 using loops of elastic material 6050. As an alternative to the hole 6018, a groove (not illustrated) may be provided on the breathing mask 6022 that is similar to the loops 6024. Another alternative to the hole 6018 is to provide half of a hook and loop fastener on the mask and the other half on the strap 6020 (not illustrated). For example, hooks could be provided on the breathing mask 6022 with loops provided on the strap 6020. Another alternative is to attach the strap 6020 to the breathing mask 6022 using adhesive.

A benefit of the loops 6024 is that the strap 6020, which may be referred to as side straps because there are strap portions on each side of a patient's face or head, may be length adjustable. Such side straps may require a higher force for certain mask types (such as a nasal cradle or nasal pillows mask), compared to a full face mask or nasal mask. The loops 6024 or a buckle may be provided at the distal end of the side strap proximal to but lower than the patient's temple. The location of the buckle preferably avoids bone and abuts against a fleshy part of the patient's face, in use, for comfort purposes in case the patient sleeps on their side. Also, this buckle location may enable the side strap to curve and closely follow the patient's cheeks, which may be sleeker and aesthetically pleasing. Preferably the buckle is not located too high as it gets too close to the eyes, which may be distracting and/or uncomfortable to the patient. Providing the loops 6024 or a buckle on the strap 6020 may be preferable to providing the loops 6024 or a buckle on the mating component because this arrangement may be more intuitive to a user.

FIGS. 5A-5N illustrate alternative headgear 6000 in various stages of assembly.

FIG. 5A illustrates a strap section 6052, which illustrated generally as a trapezoid, but any shape with one or more edges may be used as necessary to achieve a desired overall shape of the headgear 6000. The material of the strap section 6052 can be any suitable material, but is an example of the mesh material 6030 illustrated with multiple types of layers (e.g., a spacer mesh material). The topmost layer is illustrated to include relatively large openings 6054 surrounded by a relatively tight weave 6056 (e.g., a weave with relatively smaller openings between fibres). The layer immediately beneath (visible through the relatively large openings 6054) is illustrated as a weave that is substantially uniform with intermediate sized openings 6058 between the fibres. The reverse side may be of sufficiently tight weave that any openings between fibres are not visible at the scale to which FIG. 5A is illustrated. The strap section 6052 includes a first edge 6060, a second edge 6062, a third edge 6064 and a fourth edge 6064.

FIG. 5B illustrates the strap section 6052 after the first edge 6060 is covered by a V-shaped fold 6010 of another material (e.g., second flexible material 6008) but prior to trimming. FIG. 5C illustrates after trimming. FIG. 5D illustrates the strap section 6052 from the opposite side relatively to FIG. 5C. FIGS. 5A-5D illustrate the mesh material 6030 in detail. The following figures simplify the detailed illustration by substituting a pattern for the detailed illustration of the mesh layers described above with respect to FIG. 5A.

FIG. 5E illustrates various components of headgear (e.g., left crown piece 6068, right crown piece 6070, top crown piece 6072, bottom left strap piece 6074, top left strap piece 6076, bottom right strap piece 6078 and top right strap piece 6080) placed flat and adjacent to one another prior to assembly. As illustrated, the left crown piece 6068, right crown piece 6070 and top crown piece 6072 are made from a first material (e.g., spacer mesh) with a V-shaped fold 6010 of material applied along one edge of each piece. The bottom left strap piece 6074, top left strap piece 6076, bottom right strap piece 6078 and top right strap piece 6080 are made from another material (e.g., spacer fabric UBL-Un-Broken Loop-material) but does not include a V-shaped fold covering an edge. Each of the bottom left strap piece 6074, top left strap piece 6076, bottom right strap piece 6078 and top right strap piece 6080 include a section of hook material 6048 so that the respective sections can be folded back on and adhered to themselves.

FIG. 5F illustrates an exemplary joint 6082 between two of the pieces of FIG. 5E. As illustrated, the joint includes a zig-zag stitch connecting abutting edges. However, other joining arrangements can be provided. For example, the components could be overlapped (instead of abutting) and joined, and the joining process can be any suitable joining process. For example, the joining process could include welding, adhesive, or alternative stitching.

FIG. 5G illustrates the components of FIG. 5E where all adjacent components have been joined together (e.g., stitched together).

FIG. 5H illustrates two stages of a process of covering joints between adjacent headgear components. At the upper joint 6082a, only the top (visible) side of the joint has been covered by the second material 6008. At the lower joint 6082b, the second material 6008 is looped around a length of the joint 6082b to cover both the front and back sides of the lower joint 6082b as well as the ends of the joint.

FIG. 5I illustrates the assembly of FIG. 5G except that all of the joints 6082 have been covered by the second material 6008 similar to the lower joint 6082b in FIG. 5H. FIG. 5J is substantially the same as FIG. 5I except that all of the portions of the second material 6008 have been trimmed of excess material.

FIG. 5K illustrates the headgear 6000 after two additional steps have been performed. First, another V-shaped fold 6010 of the second material 6008 has been applied all along an edge 6086 of the headgear 6000 that forms and opening 6088 that fits around a region of a user's head that includes the parietal and occipital bones (e.g., the top, back area of the user's head). Second, a final joint 6090 is formed so that the bottom left strap piece 6074 and bottom right strap piece 6078 are joined together to complete the opening 6088.

FIG. 5L illustrates the final joint 6090 covered with the second material prior to trimming and FIG. 5M illustrates the headgear 6000 after all assembly steps. With this order of assembly, any joints that can contact the user and potentially cause irritation are covered and/or minimized.

FIG. 5N illustrates the headgear 6000 attached to a patient interface 3000 by way of an intermediate strap arrangement 7000. The intermediate strap arrangement 7000 extends along a side of the patient's head with a substantially T-shaped portion 7002 where the "top" of the T-shape includes loops 7004 that cooperate with the top right strap piece 6080 and the bottom right strap piece 6078 (by way of the hook material 6048-not visible-attaching to the UBL portion of the straps) to connect the headgear 6000 to the intermediate strap arrangement 7000. A similar arrangement may be provided on the left side of the user's head with the top left strap piece 6076 and the bottom left strap piece 6071. With this arrangement, a portion of the headgear 6000 extends above the user's ear and another portion extends below the user's hear. With the adjustable nature both above and below the ear, a wide range of head and/or face shapes and/or sizes can be accommodated. Together, the headgear 6000 and the intermediate strap arrangement 7000 form an example of a positioning and stabilising structure 3300.

Although FIGS. 5A-5N illustrate specific materials, joints, etc. in specific locations, the present technology can be applied to other configurations. For example, material other than spacer mesh could be used for the left crown piece 6068, right crown piece 6070 and top crown piece 6072, and/or the joints could be located elsewhere.

At least the disclosure associated with FIGS. 5A-5N may provide a very light-weight headgear (which may also be fast drying after washing and more breathable), which contributes to a light-weight mask and hence improved patient comfort. This light-weight headgear may be achieved by the disclosed joining of the spacer mesh (e.g., spacer mesh fabric) material to the spacer fabric UBL material, and ensuring patient comfort by finishing the edges of the headgear straps to avoid rough edges irritating the skin and ensure longevity of the headgear by preventing fraying of the material at the edges if they were not finished. Spacer mesh material has various advantages but it may be difficult or impractical to finish edges of spacer mesh material using conventional ultrasonic welding techniques. The present technology provides a solution to this problem in that the all edges of the headgear may be finished in a manner that may be more comfortable and less likely to fray.

Various effects may be optimized with the headgear-related technologies discussed above. For example, by altering the thickness of the second flexible material 6008 applied in the V-shaped fold 6010, and/or the thickness of adhesive used to adhere the second flexible material 6008 in the V-shaped fold 6010, the hand feel and stiffness can be optimized. For example, if the second flexible material 6008 and adhesive are relatively thin, a soft hand feel and flat seem may be achieved but the headgear may retain its overall shape relatively poorly. If the second flexible material 6008 and adhesive are relatively thick, the headgear may hold its shape well but be too hard to be comfortable.

4.4 Glossary

For the purposes of the present technology disclosure, in certain forms of the present technology, one or more of the following definitions may apply. In other forms of the present technology, alternative definitions may apply.

4.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Respiratory Pressure Therapy (RPT): The application of a supply of air to an entrance to the airways at a treatment pressure that is typically positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.4.2 Anatomy of the face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 4.4.3 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.4.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.4.5 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.4.6 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. In addition to or in the alternative to that described above, the headgear may comprise a collection of one or more struts, ties and stiffeners configured to locate and retain a patient interface in position on a patient's face for delivery of respiratory therapy. Some ties may be formed of a soft, flexible, elastic material such as a laminated composite of foam and/or fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows a flow of air from an interior of the mask, or conduit, to ambient air to allow clinically effective washout of exhaled gases. For example, a clinically effective washout may involve a flow rate of about 10 litres per minute to about 100 litres per minute, depending on the mask design and treatment pressure.

4.4.7 Terms used in relation to patient interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:
  Readily conforming to finger pressure.
  Unable to retain its shape when caused to support its own weight.
  Not rigid.
  Able to be stretched or bent elastically with little effort.
  The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

4.4.8 Curvature

Products in accordance with the present technology may comprise one or more real three-dimensional structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.4.8.1 Curvature in one dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.4.8.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

REFERENCE SIGNS LIST 1000 patient
3000 patient interface
3100 seal-forming structure
3200 plenum chamber
3300 positioning and stabilising structure
3400 vent
3600 connection port
3700 forehead support
4000 RPT device
4170 air circuit
6000 headgear
6002 strap
6002a strap
6002b strap
6004 first flexible material
6006 elongate edge
6007 second elongate edge
6008 second flexible material
6010 V-shaped fold
6012 third flexible material
6014 fourth flexible material
6016 connection
6018 hole
6020 strap
6022 breathing mask
6026 alternative second flexible material
6028 adhesive film
6030 mesh material
6032 first flexible strap portion
6034 second flexible strap portion
6036 intersection
6038 first layer
6040 second layer
6042 third layer
6044 adhesive
6046 Y-shaped profile
6048 hook material
6050 elastic material
6052 strap section
6054 relatively large openings
6056 relatively tight weave
6058 intermediate openings
6060 first edge
6062 second edge
6064 third edge
6066 fourth edge
6068 left crown piece
6070 right crown piece
6072 top crown piece
6074 bottom left strap piece
6076 top left strap piece
6078 bottom right strap piece
6080 top right strap piece
6082 joint
6082a upper joint
6082b lower joint
6084 excess material
6086 edge
6088 opening
6090 final joint
7000 intermediate strap arrangement
7002 substantially T-shaped portion
7004 loops

The invention claimed is:

1. A patient interface for delivering pressurized breathing gas to a patient, the patient interface comprising:
a breathing mask configured to interface with the patient to deliver breathable gas to the patient's airways; and
a headgear assembly configured to support the breathing mask on the patient's face, the headgear assembly including:
a first flexible strap portion with a first end;
a second flexible strap portion with a second end attached to and fixed relative to the first end at a joint to form a strap such that the first flexible strap portion and the second flexible strap portion do not overlap one another along a majority of the strap, the first flexible strap portion and the second flexible strap portion defining an elongate edge of the strap; and
a covering material folded over and running along the elongate edge of the strap including extending over the joint formed by attaching the second end of the second flexible strap portion to the first end of the first flexible strap portion.

2. The patient interface according to claim 1, wherein the first end and the second end define short edges transverse to the elongate edge, and the covering material covers at least one of the short edges.

3. The patient interface according to claim 2, wherein the covering material covers an entire length of the at least one short edge.

4. The patient interface according to claim 1, wherein the first flexible strap portion has different material properties than the second flexible strap portion.

5. The patient interface according to claim 1, wherein the first flexible strap portion is configured to stretch more than the second flexible strap portion.

6. The patient interface according to claim 1, wherein the first flexible strap portion is elastic and the second flexible strap portion is non-elastic.

7. The patient interface according to claim 1, wherein the first flexible strap portion comprises a spacer fabric.

8. The patient interface according to claim 1, wherein the second flexible strap portion comprises two layers of material at the second end and the first end is inserted between and connected to the two layers.

9. The patient interface according to claim 8, wherein one of the two layers of material comprises a first half of a hook and loop fastener.

10. The patient interface according to claim 9, wherein the second flexible strap portion further comprises a second half of hook and loop fastener configured such that the second flexible strap portion can be folded to attach the first half of the hook and loop fastener to the second half of the hook and loop fastener.

11. The patient interface according to claim 8, wherein the two layers of material are connected away from the second end beyond the first end.

12. The patient interface according to claim 11, wherein the two layers form a Y-shape into which the first end is inserted.

13. The patient interface according to claim 8, wherein the two layers of material are connected to each other and to the first end by layers of adhesive.

14. The patient interface according to claim 1, wherein the strap comprises three legs that intersect to form a Y-shaped profile.

15. The patient interface according to claim 1, further comprising a second strap releasably connected to the strap.

16. The patient interface according to claim 15, wherein the second strap comprises a connection for the breathing mask.

17. The patient interface according to claim 16, wherein the connection comprises a hole through which the breathing mask is configured to pass.

18. The patient interface according to claim 17, wherein the hole is configured to pass around an outer perimeter of a section of the breathing mask.

19. The patient interface according to claim 1, wherein the breathing mask is a nasal cradle mask.

20. The patient interface according to claim 1, wherein the breathing mask is a nasal pillows mask.

* * * * *